United States Patent
Imran

(10) Patent No.: US 11,833,319 B2
(45) Date of Patent: Dec. 5, 2023

(54) PROPULSIVE DRUG DELIVERY FROM A SWALLOWABLE DEVICE INTO A PATIENTS INTESTINAL TRACT

(71) Applicant: Rani Therapeutics, LLC, San Jose, CA (US)

(72) Inventor: Mir Imran, Los Altos Hills, CA (US)

(73) Assignee: Rani Therapeutics, LLC, San Jose, CA (US)

( * ) Notice: Subject to any disclaimer, the term of this patent is extended or adjusted under 35 U.S.C. 154(b) by 727 days.

(21) Appl. No.: 16/805,583

(22) Filed: Feb. 28, 2020

(65) Prior Publication Data

US 2020/0276426 A1 Sep. 3, 2020

Related U.S. Application Data

(60) Provisional application No. 62/821,250, filed on Mar. 20, 2019, provisional application No. 62/812,867, filed on Mar. 1, 2019.

(51) Int. Cl.
*A61M 31/00* (2006.01)
*A61M 5/142* (2006.01)
(Continued)

(52) U.S. Cl.
CPC ...... *A61M 31/002* (2013.01); *A61M 5/14276* (2013.01); *A61M 25/0116* (2013.01);
(Continued)

(58) Field of Classification Search
None
See application file for complete search history.

(56) References Cited

U.S. PATENT DOCUMENTS 8,562,589 B2 10/2013 Imran
8,734,429 B2 5/2014 Imran et al.
(Continued)

FOREIGN PATENT DOCUMENTS

CN 108686292 A 10/2018
EP 0 132 102 A2 1/1985
(Continued)

OTHER PUBLICATIONS

Yu et al. A Smart Capsule with GI-Tract-Location-Specific Payload Release. IEEE Trans Biomed Eng. Sep. 2015; 62(9): 2289-95. doi: 10.1109/TBME.2015.2418340. Epub Apr. 20, 2015 (Year: 2015).*
(Continued)

*Primary Examiner* — Jenna Zhang
(74) *Attorney, Agent, or Firm* — Foley & Lardner LLP

(57) ABSTRACT

Embodiments of the invention provide swallowable devices, preparations, and methods for delivering drugs and other therapeutic agents within the GI tract. Particular embodiments provide a swallowable device such as a capsule for delivering drugs or other therapeutic agents (TA) into a wall of the GI tract such as the stomach or small intestine. The swallowable device comprises a sensor, a combustible propellant (CP) and a therapeutic agent preparation (TAP) comprising at least one TA. The sensor triggers the CP to ignite and propel the TAP into the wall of the GI tract in response to an external condition or change in external condition. Embodiments of the invention are particularly useful for orally delivering drugs or other TAs which are degraded within the GI tract and require parenteral injection.

22 Claims, 8 Drawing Sheets

(51) Int. Cl.
*A61M 25/10* (2013.01)
*A61M 25/01* (2006.01)

(52) U.S. Cl.
CPC ............ *A61M 25/10* (2013.01); *A61M 31/00* (2013.01); *A61M 31/007* (2013.01); *A61M 2205/3331* (2013.01); *A61M 2205/3344* (2013.01); *A61M 2205/3368* (2013.01); *A61M 2205/8231* (2013.01); *A61M 2210/1042* (2013.01); *A61M 2210/1053* (2013.01); *A61M 2230/208* (2013.01); *A61M 2230/60* (2013.01)

(56) References Cited

U.S. PATENT DOCUMENTS

| | | | |
|---|---|---|---|
| 8,764,733 | B2 | 7/2014 | Imran |
| 8,809,269 | B2 | 8/2014 | Imran |
| 8,809,271 | B2 | 8/2014 | Imran |
| 8,846,040 | B2 | 9/2014 | Imran |
| 8,969,293 | B2 | 3/2015 | Imran |
| 8,980,822 | B2 | 3/2015 | Imran |
| 9,149,617 | B2 | 10/2015 | Imran |
| 9,259,386 | B2 | 2/2016 | Imran |
| 9,283,179 | B2 | 3/2016 | Imran |
| 9,284,367 | B2 | 3/2016 | Imran |
| 9,402,806 | B2 | 8/2016 | Imran |
| 9,402,807 | B2 | 8/2016 | Imran |
| 9,415,004 | B2 | 8/2016 | Imran |
| 9,629,799 | B2 | 4/2017 | Imran |
| 9,757,548 | B2 | 9/2017 | Imran |
| 9,861,683 | B2 | 1/2018 | Imran |
| 10,098,931 | B2 | 10/2018 | Morales et al. |
| 10,220,003 | B2 | 3/2019 | Imran et al. |
| 10,227,403 | B2 | 3/2019 | Imran et al. |
| 10,300,259 | B2 | 5/2019 | Ziaie et al. |
| 10,603,275 | B2 | 3/2020 | Imran et al. |
| 10,689,460 | B2 | 6/2020 | Imran et al. |
| 11,565,095 | B2 | 1/2023 | Imran |
| 2003/0114789 | A1* | 6/2003 | Haar ................ A61M 5/30 604/69 |
| 2004/0253304 | A1 | 12/2004 | Gross et al. |
| 2007/0010709 | A1 | 1/2007 | Reinschke |
| 2007/0055200 | A1 | 3/2007 | Gilbert |
| 2007/0250132 | A1 | 10/2007 | Burnett |
| 2010/0286628 | A1 | 11/2010 | Gross |
| 2011/0017335 | A1 | 1/2011 | Blake |
| 2011/0160699 | A1* | 6/2011 | Imran ................ A61K 38/2235 604/93.01 |
| 2011/0208270 | A1 | 8/2011 | Imran et al. |
| 2015/0064241 | A1 | 3/2015 | Conrad |
| 2016/0114142 | A1 | 4/2016 | Ziaie et al. |
| 2016/0235663 | A1* | 8/2016 | Zou ................ A61M 31/002 |
| 2016/0256106 | A1 | 9/2016 | Krasnow et al. |
| 2017/0265598 | A1 | 9/2017 | Beers et al. |
| 2017/0291019 | A1 | 10/2017 | Dang et al. |
| 2018/0251537 | A9 | 9/2018 | Imran et al. |
| 2019/0062451 | A9 | 2/2019 | Imran et al. |
| 2020/0276425 | A1 | 9/2020 | Imran |
| 2023/0137442 | A1 | 5/2023 | Imran |

FOREIGN PATENT DOCUMENTS

| | | |
|---|---|---|
| EP | 2238885 A1 | 10/2010 |
| WO | WO-2008/053396 A2 | 5/2008 |
| WO | WO-2018213582 A1 | 11/2018 |
| WO | WO-2020180745 A1 | 9/2020 |
| WO | WO-2020180746 A1 | 9/2020 |

OTHER PUBLICATIONS

Pi et al. A novel micro-fabricated thruster for drug release in remote controlled capsule. Sensors and Actuators A: Phyical. vol. 159. Issue 2. May 2010. pp. 227-232. DOI:10.1016/j.sna.2010.03.035 (Year: 2010).*

Sun S, Ma S, Zhao B, Zhang G, Luo Y. A Facile Way to Prolong Service Life of Double Base Propellant. Materials. 2018; 11(11): 2236 (Year: 2018).*

Fiume, et al. Safety Assessment of Nitrocellulose and Collodion as Used in Cosmetics. Int J Toxicol. Jul. 2016;35(1 Suppl):50S-9S. doi: 10.1177/1091581816651607.

International search report with written opinion dated May 15, 2020 for PCT/US2020/020540.

International search report with written opinion dated Jun. 11, 2020 for PCT/US2020/020544.

Laulicht, et al. Understanding Gastric Forces Calculated From High-Resolution Pill Tracking. Proc Natl Acad Sci USA. May 4, 2010;107(18):8201-8206. doi: 10.1073/pnas.1002292107. Epub Apr. 19, 2010.

Pi, et al. A novel micro-fabricated thruster for drug release in remote controlled capsule. Sensors and Actuators A: Physical. vol. 159. Issue 2. May 2010. pp. 227-232. DOI:10.1016/j.sna.2010.03.035.

Steiger, et al. Ingestible electronics for diagnostics and therapy. Nature Reviews Materials. Dec. 17, 2018. vol. 4. pp. 83-98. DOI:10.1038/s41578-018-0070-3.

Yu, et al. A Smart Capsule With GI-Tract-Location-Specific Payload Release. IEEE Trans Biomed Eng. Sep. 2015;62(9):2289-95. doi: 10.1109/TBME.2015.2418340. Epub Apr. 20, 2015.

Notice of Allowance on U.S. Appl. No. 16/805,317 dated Sep. 29, 2022.

Pix et al: "A novel micro-fabricated thruster for drug release in remote controlled capsule", Sensors and Actuators A: Physical, Elsevier BV, NL, vol. 159, No. 2, May 1, 2010 (May, 1, 2010), pp. 227-232, XP027037993.

* cited by examiner

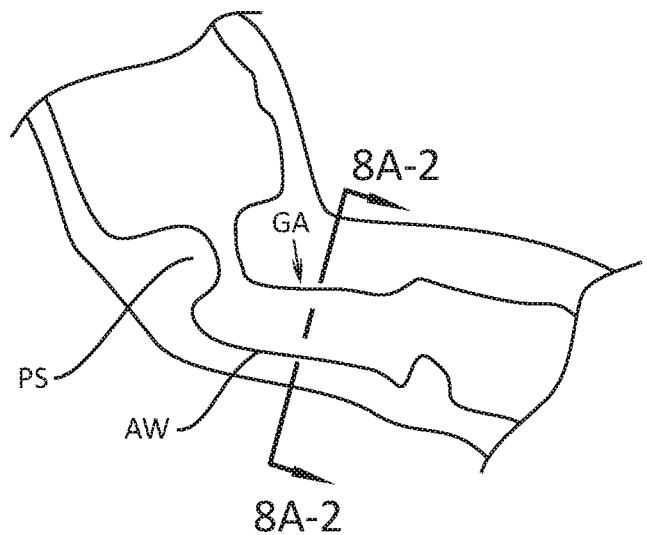
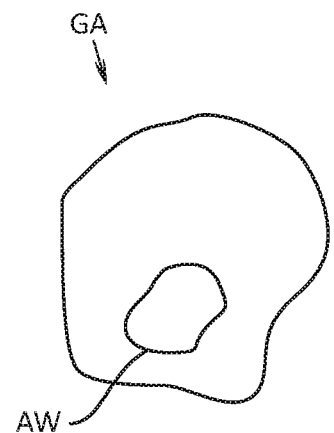
FIG. 8A-1  FIG. 8A-2
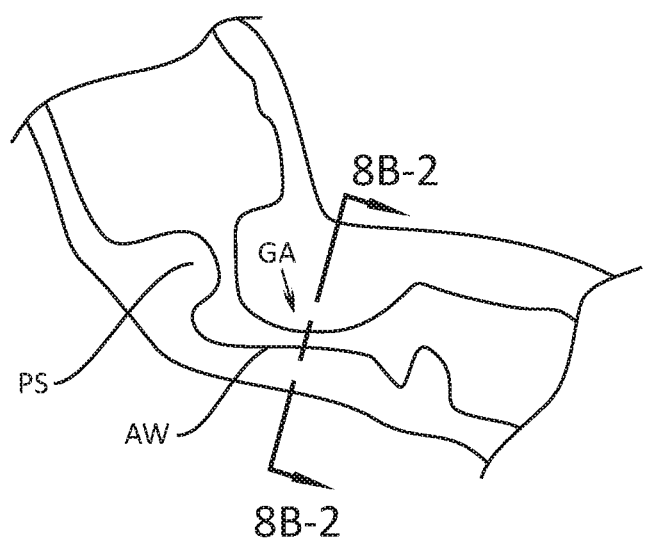
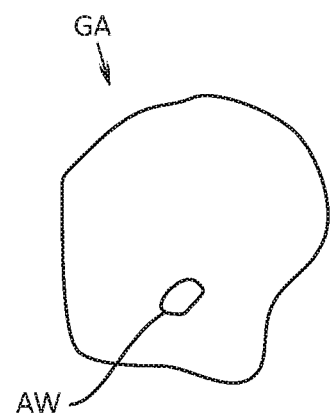
FIG. 8B-1  FIG. 8B-2

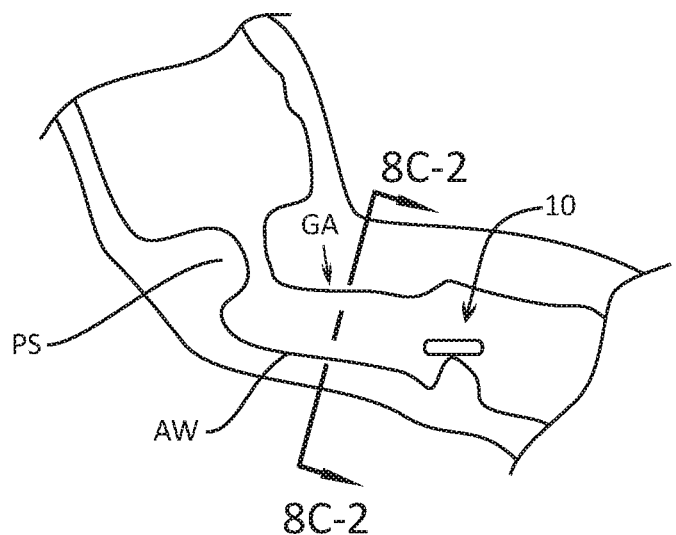
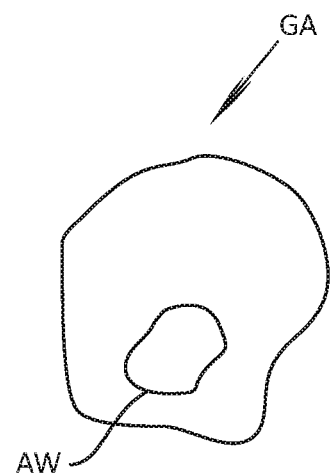
FIG. 8C-1
FIG. 8C-2
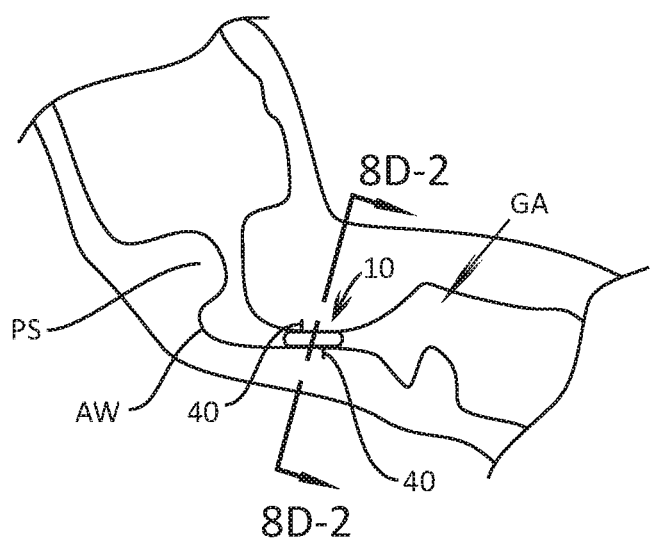
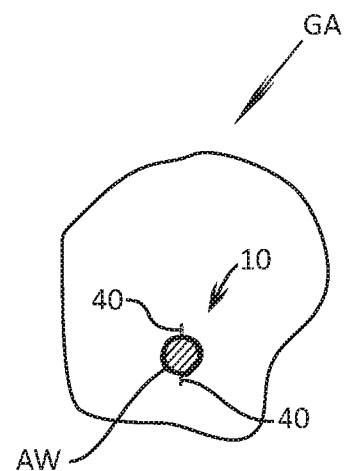
FIG. 8D-1
FIG. 8D-2

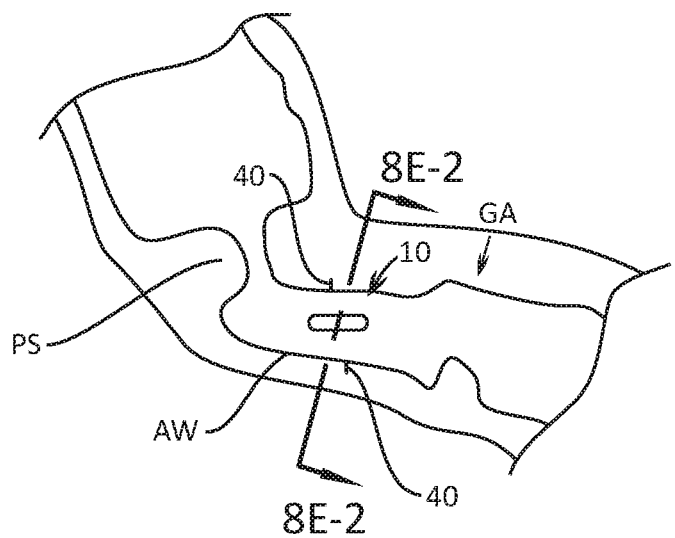
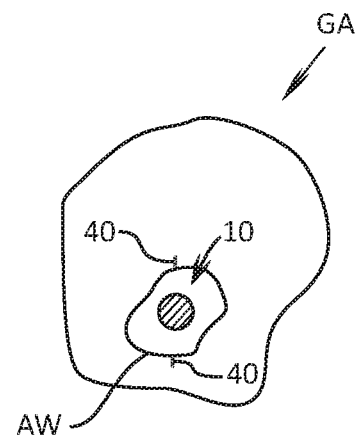
FIG. 8E-1
FIG. 8E-2
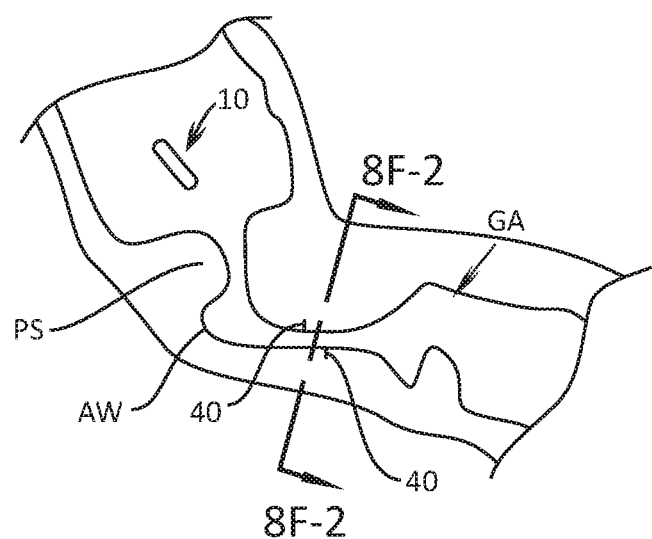
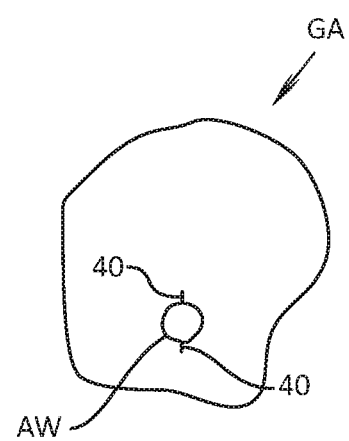
FIG. 8F-1
FIG. 8F-2

PROPULSIVE DRUG DELIVERY FROM A SWALLOWABLE DEVICE INTO A PATIENTS INTESTINAL TRACT

CROSS-REFERENCES TO RELATED APPLICATION

This application claims priority to, and the benefit of, U.S. Provisional Patent Application Ser. Nos. 62/821,250 filed on Mar. 20, 2019, and U.S. Provisional Application No. 62/812,867, filed on Mar. 1, 2019, the full disclosures of both of which are both incorporated herein by reference for all purposes.

BACKGROUND

1. Technical Field

The present invention relates to swallowable drug delivery devices. More specifically, the present invention relates to swallowable drug delivery devices for delivering therapeutic agents into the gastric antrum or other portion of the stomach wall.

2. Background Discussion

While there has been an increasing development of new drugs in recent years for the treatment of a variety of diseases, many drugs including proteins, antibodies, peptides, and other labile medicaments have limited use because they cannot be given orally and thus typically require intravenous or other form of parenteral administration (e.g., intramuscular, etc.) to avoid degradation. The inability to deliver the drug orally may arise from any one of a number of reasons, including poor oral toleration with complications including gastric irritation and bleeding, breakdown/degradation of the drug compounds in the stomach, and poor, slow or erratic absorption of the drug.

Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery.

Thus, there is a need for additional, alternative, and improved methods, devices, and articles for the oral delivery of drugs and other therapeutic agents. In particular, it would be desirable to provide delivery vehicles and constructions that allow the oral administration of a drug and subsequent injection or other delivery of the drug into targeted regions of a patient's gastrointestinal (GI) tract. For example, it would be desirable to provide methods, devices, and articles for the injection of drugs directly into wall regions of the patient's GI tract, where the timing, location, and injection force are able to be more precisely controlled. At least some of these objectives will be met by the description detailed hereinafter.

US2003/0114789, US2007/0055200, and US2017/0265598 describe an implantable system that injects a drug into a patient's antrum to induce contractions as part of an obesity treatment. Patents and published patent applications having common inventorship and/or common ownership with the present application that describe swallowable capsules for injecting drugs into an intestinal or other wall in the GI tract include U.S. Pat. No. 9,149,617; US2011/0208270; and US20120010590. Published PCT Application WO2018/213582 describes a capsule with a spring-loaded medicament structure for injection drugs into a stomach wall.

BRIEF SUMMARY

Embodiments, of the present invention provide devices, systems, articles, formulations, kits, and methods for delivering drugs and other therapeutic agents into a wall of a patient's gastro-intestinal tract including the stomach, the gastric antrum, the duodenum, the small intestines, and the like. In particular, embodiments of the present invention provide swallowable capsules and other devices suitable for the delivery of drugs and other labile therapeutic agents that are poorly absorbed, poorly tolerated, and/or degraded within the gastrointestinal (GI) tract, such as proteins, polypeptides and antibodies. The proteins and antibodies may include one or more biologics known in the pharmaceutical and biosimilar arts such as insulin, tnf-$\alpha$ antibodies and interleukin antibodies (e.g., interleukin 17 antibodies). PCSK9 antibodies and various clotting factors (e.g., Factors VII, VIII, IX, Factor X, etc.). While particularly useful for the injection of such labile therapeutic agents into a wall of the gastric antrum, embodiments the present invention will also find use with other medicaments and introduction into other locations in the GI tract such as the walls of the small intestine, large intestine, buccal surfaces in the mouth and elsewhere in the patient's body.

The devices and methods of the present invention incorporate propulsive drivers for injecting solid dosage medicaments and other therapeutic agents into luminal walls of the GI tract (e.g., the stomach, small intestine, etc.), where the propulsive drivers typically comprise a combustible propellant and an igniter. The igniter may be configured to ignite the combustible propellant in response to a change in a condition external to the capsule, such as pH, pressure, wall proximity, conductivity, or the like.

In many embodiments, the swallowable devices of the present invention may include sensors, such as pressure sensors, pH sensors, conductivity sensors, or other mechanisms that can detect a position of the swallowable device within the GI tract. Particular embodiments comprise a swallowable device, such as a capsule, for delivering drugs and other therapeutic agents into the wall of the patient's stomach, gastric antrum, duodenum, and/or small intestines. For example, the device may be a swallowable capsule configured to detect or respond to a change in conductivity indicative of presence in the stomach, to a change in pressure exerted on an exterior of the device by contractions of the antrum, and/or a change in pH to detect entry into the duodenum and small intestines. Once the capsule has arrived at a target location in the GI tract, the propulsive driver can be triggered to inject or otherwise deliver the medicament while the capsule is in that location. Such swallowable capsules and other devices may be further configured to self-align when in a particular luminal location, such as the antrum, the duodenum, or small intestines, so that the medicament is injected from the capsule in a predetermined direction into an adjacent wall of the GI tract. Preferably the direction is perpendicular to the wall of the antrum or other portion of the stomach or GI tract. However, other directions are also considered such as at a 45° angle.

Specific embodiments of the present invention are particularly useful for the delivery of solid dosage forms of drugs and other therapeutic agents, particularly those that would otherwise be degraded by digestive fluids in the GI tract if not delivered into GI wall tissue, while other embodiments will be useful for the delivery of liquid, gel, powder, and other conventional medicament forms. The exemplary solid dosage forms will often be self-penetrating, for example having a sharpened, pointed, tapered, or other shaped distal tip to facilitate penetration through a surface of an antral or other luminal wall of the GI tract. Such self-penetrating solid dosage forms are sometimes referred to herein as tissue-penetrating members (TPM) hereinafter. Many embodiments of the preset invention will be capable of achieving a rapid release of a drug into the blood stream via oral delivery with minimum or no degradation resulting from passage through any portion of the GI tract.

In a first aspect, a swallowable device for delivering a solid dosage therapeutic agent preparation to a patient comprises a swallowable capsule having a capsule wall. A solid dosage therapeutic agent, such as a tissue-penetrating member or TPM as described elsewhere herein, is held inside the capsule, and a propulsive driver within the capsule is arranged and configured to advance the solid dosage therapeutic agent through the capsule wall and into a wall of the gastrointestinal (GI) tract. The propulsive driver typically comprises a combustible propellant and an igniter. The igniter is typically configured to ignite the combustible propellant in response to a condition external to the capsule. Such external conditions may be static conditions, such as a pH or a temperature that remains restively constant in a specific region of the GI tract over time, or may be changing or dynamic, such as pressure that changes in particular regions of the GI tract over time as a result of peristalsis.

The condition external to the capsule may be any one of moisture, temperature, pressure, pH, proximity to a wall of the GI tract, or any other condition within the GI tract that can be sensed by a sensor or that can cause a change in the capsule that can trigger the igniter. Often, the igniter will be configured to ignite the combustible propellant in response to a change in a condition within a region of the GI tract. Conditions that change in a particular region include, for example, pressure in the antrum or small intestines, proximity to a wall of the GI tract, and the like. Alternatively, the igniter may be configured to ignite the combustible propellant in response to a static condition that is encountered as the capsule enters a particular region of the GI tract. For example, the pH in the stomach is significantly lower (about pH3) than the pH in the small intestines (about pH7-9). The igniter can be configured to ignite in response to a lowering of the pH as the swallowable capsule passes from the stomach, through the pylorus, and into the duodenum and small intestines. In still other instances, the condition may be static, and the igniter may require some time period of exposure to the condition to be triggered. For example, the igniter can be triggered by exposure to moisture in the GI tract for a time calculated to assure that the capsule as entered a target region of the GI tract.

The swallowable devices of the present invention may include a sensor embedded in the capsule wall and coupled to the igniter. In such instances, the sensor may be configured to sense the value of the external condition and to cause the igniter to ignite the combustible propellant when a threshold value or change in value of the condition is reached. Electronic sensors for measuring external pressure resulting from contact with a patient's antral wall are more specifically described herein, but additional electronic sensors measuring any of moisture, pH, temperature, and the like, may also find use.

In embodiments employing an electronic sensor, the sensor will typically produce an electrical signal representative of the sensed condition. In such instances, the igniter typically comprises a trigger circuit that receives the signal representative of the sensed condition from the sensor and that generates an ignition current that is delivered to the ignition circuit and to the combustible propellant. The ignition current will be sufficient to ignite the combustible propellant, typically by heating, glowing, sparking, or otherwise initiating combustion.

Suitable trigger circuits typically include at least a battery and a capacitor, where the battery charges the capacitor, and the capacitor discharges into the propellant after a sufficient charge has been accumulated. For example, the capacitor may discharge the accumulated current into wire filaments or other conductors embedded in the propellant, where the wire filaments produce heat sufficient to ignite the propellant as the current is discharged from the capacitor therethrough. Suitable propellants include nitrocellulose-based compositions, such as a fine-grain nitrocellulose formed into a thin sheet or layer that can be disposed beneath a piston for propelling a drug dosage, as described in more detail herein below.

The drug dosage will typically be in a solid form, more typically being in a solid form that is capable of penetrating a wall of the GI tract such as a wall of the stomach or small intestine after it has been expelled from the swallowable capsule (however, embodiments of liquid and a mixture of solid and liquid dosages are also contemplated). Examples of such solid forms, referred to as tissue-penetrating members or TPM's, are described in detail below. The solid dosage drug will usually be propelled from the swallowable capsule by a propulsive driver comprising a piston and cylinder. The combustible propellant is preferably located at a closed end or "bottom" of the cylinder, beneath the piston, where the solid dosage therapeutic agent is located on an opposed or "upper" surface of the piston. When the nitrocellulose or other combustible propellant is ignited beneath the piston, the piston will be driven forwardly from the cylinder and will drive the solid dosage therapeutic agent through a wall of the swallowable capsule so that it can penetrate a gastric wall or other wall lumen wall of the GI tract (e.g., the small intestine). Often, the solid dosage therapeutic agent will be delivered through a penetrable barrier formed in the wall of the swallowable capsule to assure that the drug can be expelled with minimum interference while protecting the drug prior to delivery. In specific embodiments, when the propellant comprises a layer of nitrocellulose (e.g., positioned at the bottom of the cylinder), the layer may have a mass in a range from about 1 to 8 mg, more preferably, about 3 mg. In other embodiments comprising a layer of nitrocellulose formed along the bottom of the cylinder, the layer of nitrocellulose comprises from 0.1 gm to 0.5 gm of nitrocellulose. Further the specific mass of nitrocellulose can be adjusted depending upon the desired GI wall into which the solid drug dosage is delivered into. Larger amounts of nitrocellulose may be used for thicker walls such as those found in antrum and lesser amounts for thinner walls such as those found in the small intestine. Adjustments in the amount of nitrocellulose may also be made for desired penetration depth of the solid drug dosage into the target GI wall. For example, larger amounts of nitrocellulose may be used to assure penetration through the small intestine and into the peritoneal wall and/or cavity.

In other preferred aspects of the swallowable device of the present invention, the swallowable capsule wall comprises a cylindrical shell, typically having a conventional drug capsule geometry with rounded or hemispherical ends at each side of the cylindrical wall. Other shapes are also contemplated including spherical, hemispherical, pyramidal and the like. The capsule wall will often be degradable over time in the patient's intestinal tract but will be sufficiently robust so that it will not degrade prior to delivery of the drug from the capsule. Other components of the swallowable device may be degradable or may be sufficiently small so that they will be expelled from the patient's intestines through normal digestive processes.

In a further aspect of the present invention, a method for delivering a therapeutic agent into a wall of a patient's intestinal tract comprises providing a swallowable capsule having the therapeutic agent preparation held therein. The patient ingests the swallowable capsule, and the capsule passes through an initial portion of the patient's GI tract while maintaining the therapeutic agent therein in a bioactive form unaffected by digestive fluids or other condition in the GI tract. After a time, a combustible propellant within the capsule will be ignited in response to an external condition within the GI tract, often a change in a sensed external condition, and the ignited propellant will inject the therapeutic agent from the capsule into a wall of the GI tract.

In specific aspects of the methods of the present invention, the combustible propellant within the capsule may be ignited in response to exposure to an external condition (e.g., a condition in the GI tract external to the capsule), often a change in condition, such as pH, pressure, proximity to a wall of the GI tract, and the like. In other specific aspects, the capsule may be ignited in response to exposure to a static condition such as moisture, temperature, pressure, pH, and the like, either for some threshold exposure time or as a result of the capsule entering a different region of the GI tract (e.g., going from the pylorus into the small intestine).

In particular embodiments of the methods of the present invention, a sensor may be provided on or in the swallowable capsule and be coupled to trigger the combustible propellant to inject the therapeutic agent into the wall of the GI tract. Exemplary sensors comprise electrical transducers incorporated into or otherwise associated with the wall of the swallowable capsule, such as pressure transducers, temperature transducers, pH transducers, optical transducers and other transducers/sensors capable of detecting substances or conditions relevant to the delivery of drugs within the GI tract. Such electrical sensors typically generate an electrical signal that is configured to electrically trigger ignition of the combustible propellant in order to inject the therapeutic agent into the wall of the GI tract.

In alternative embodiments, the sensor may comprise a mechanical or fluidic transducer, component, mechanism, or the like, incorporated into or otherwise associated with the wall of the swallowable capsule. Such mechanical or fluidic transducers will typically be coupled to mechanically or fluidically trigger the combustible propellant to inject the therapeutic agent into the wall of the GI tract. Such mechanical or fluidic transducers will typically be coupled to a mechanical ignitor capable of producing heat, sparking, or other mechanical energy capable of igniting the combustible propellant.

In many embodiments of the methods of the present invention, igniting the combustible propellant comprises triggering a circuit that generates an ignition current and delivers the ignition current to the combustible propellant. Exemplary triggering circuits include a capacitor and a battery, where the capacitor is charged by the battery and discharges current from the capacitor after a charge sufficient to ignite the combustible propellant has been accumulated in the capacitor.

Exemplary ignitors for the combustible propellant include conductive wire filaments such as a tungsten, nichrome or alloy thereof embedded in or otherwise positioned in or around the combustible propellant (e.g., nitrocellulose), where the current charge produces heat or sparking within the filaments sufficient to ignite the propellant as the current is discharged from the capacitor through the filaments.

In many embodiments, the combustible propellant is disposed at a bottom of a cylinder beneath a piston, where the solid dosage therapeutic agent is located on an upper surface of the piston (i.e., a surface on the side of the piston opposite to that of the combustible propellant). Ignition of the combustible propellant then causes a combustion and expansion of gases and materials beneath the piston in order to drive the piston in a direction that advances the solid dosage therapeutic agent through a wall of the capsule and into target tissue within a wall of the GI tract.

In another aspect, a swallowable device for delivering a therapeutic agent preparation into an antral wall of a patient's stomach comprises a capsule, a therapeutic preparation in the capsule, a sensor, and an ejector operably coupled to the tissue-penetrating therapeutic penetration. The capsule is typically sized to pass through the patient's GI tract and usually has a wall including opposed side portions and opposed end portions. Such capsules typically have an elongated shape configured to longitudinally orient within a lumen of the GI tract, such as the antrum. The therapeutic preparation in the capsule comprises a therapeutic agent shaped as a tissue-penetrating member, and a sensor disposed on a side wall portion of the capsule is configured to sense a condition external to the capsule and produce an output. The ejector is operatively coupled to both the tissue-penetrating member and the sensor and is configured to trigger combustion of a propellant to eject the tissue-penetrating member through the capsule wall into a wall of the GI tract responsive to output from the sensor.

In yet another aspect, a swallowable device for delivering a therapeutic agent preparation into an antral wall of a patient's stomach comprises a capsule, a therapeutic preparation, a sensor, a logic circuit, and an ejector. The capsule is sized to pass through the patient's intestinal tract and has a wall that includes opposing side portions and opposing end portions. The capsule has an elongated shape, and the geometry of the capsule is configured to longitudinally orient within a lumen of the GI tract during a peristaltic contraction of the stomach, such that a side portion of the capsule wall is brought into adjacency with the wall of the GI tract, typically a wall of the antrum. The therapeutic preparation in the capsule comprises a therapeutic agent shaped as a tissue-penetrating member. The sensor is disposed in a side wall portion of the capsule wall and configured to sense a condition external to the capsule and generate an electrical output. The logic circuit is configured to analyze the electrical output from the sensor and generate a trigger signal when a change in external condition is detected, such as a change in pH, a change in pressure, a change in proximity to the GI tract wall, or the like. The ejector is operatively coupled to both the tissue-penetrating member and the sensor, and the ejector is configured to trigger combustion of a propellant to eject the tissue-penetrating member through the capsule wall into a wall of the GI tract responsive to the electrical output from the sensor.

In some embodiments, the TPM contains the drug or other therapeutic agent and is configured to be inserted into the antral or other intestinal wall by expansion of a driving member, such as a propulsive element, a delivery balloon, or other expandable delivery means. The TPM typically comprises a shaft including a proximal portion that may be detachably coupled to the driving member or intermediary member to the driving member (e.g., a shaft), a tissue-penetrating distal portion, and optionally a retaining feature for retaining the tissue-penetrating member within the antral or other region of the intestinal wall. The tissue-penetrating end will typically be tapered, chamfered, or otherwise formed or sharpened to enhance tissue penetration when driven into tissue such as the antral wall, small intestine wall or other lumen wall of the GI tract. The tissue retention member may be a hook, barb, bifurcation, or the like that allows advancement into the tissue but resists retraction from the tissue. The TPM need not include a retaining feature, but instead can have a shape or otherwise be configured to be retained in the stomach or intestinal wall without the retaining feature.

The TPM will typically be formed at least in part from a therapeutic agent preparation including a drug or other therapeutic agent that is configured to dissolve or otherwise be absorbed within the antrum, stomach wall, intestinal wall, or other lumen wall of the GI tract so as to deliver the therapeutic agent preparation to the patient's blood stream. The therapeutic agent preparation may also include one or more pharmaceutical excipients known in the art, e.g., disintegrants, binders etc. The TPM is desirably configured to penetrate a selected distance into the intestinal wall so as to deliver therapeutic agent to a particular tissue layer of the intestinal wall, for example the mucosal layer, submucosal layer, etc. This can be achieved through the use of stops positioned on the TPM shaft and/or configuring the TPM shaft to bend or even shear once it penetrates a selected distance in the intestinal wall. It may also be achieved by beveling or otherwise angling the tip of the TPM so it veers or angles horizontally once it enters tissue.

Typically, the drug or other therapeutic agent delivered by the TPM will be mixed in with a biodegradable polymer such as PEO (polyethylene oxide), PLA (Polylactic acid), PLGA, and/or a sugar such as maltose. In such embodiments, the TPM may comprise a substantially heterogeneous mixture of drug and biodegradable polymer. Alternatively, the penetrating member may include a portion formed substantially from biodegradable polymer and a separate section or compartment that is formed from or contains the drug or other therapeutic agent. For example, in one embodiment the TPM may comprise an outer shell of biodegradable material with a hollow core (or other hollow portion) that is fitted with a slug (e.g., cylinder shaped) of the therapeutic agent. The tip or tissue-penetrating portion of the TPM can include a harder material such as a sugar or a metal (e.g. magnesium or magnesium alloy) so as to be able to more readily penetrate tissue. Once placed in the stomach (e.g., antrum) wall, intestinal wall (e.g. the small intestine) or other wall of the GI tract, the tissue-penetrating member is degraded by the interstitial fluids within the wall tissue, the drug dissolves in those fluids and is absorbed into the blood stream by the capillaries in or around the particular intestinal wall (e.g., the stomach, small intestine). The TPM will also typically include one or more tissue retaining features such as a barb or hook to retain the penetrating member within the tissue of the intestinal wall after advancement. The retaining features can be arranged in various patterns to enhance tissue retention such as two or more barbs symmetrically distributed around the member shaft. However, the TPM can also be retained in the intestinal through other means such as by a reverse taper or other shape. The reverse taper shape may also be combined with one or more retaining features to further enhance retention.

The drug or other therapeutic agent can be in solid form and then formed into the shape of the tissue-penetrating member using molding or other like method or may be in solid or liquid form and then added to the biodegradable polymer in liquid form with the mixture then formed into the TPM using molding or other forming method known in the polymer arts. Desirably, embodiments of the tissue-penetrating member comprising a drug and degradable polymer are formed (e.g., cured) at temperatures that do not produce any substantial thermal degradation of the drug including drugs such as various peptides and proteins. This can be achieved through the use of room-temperature curing polymers and room temperature molding and solvent evaporation techniques known in the art. In particular embodiments, the amount of thermally degraded drug within the tissue-penetrating member is desirably less than about 10% by weight, more preferably less than 5% and still more preferably, less than 1%. The thermal degradation temperatures for a particular drug are known or can be determined using methods known in the art and then this temperature can be used to select and adjust the particular polymer processing methods (e.g., molding, curing. solvent evaporation etc.).

In other aspects, the present invention provides therapeutic agent preparations for delivery into the wall of the small intestine (or other wall of a lumen in the GI tract such as the stomach) using embodiments of the swallowable device described herein. The preparation comprises a therapeutically effective dose of at least one therapeutic agent (e.g., insulin, incretin, an anti-seizure compound, NSAIDs, an antibiotic etc.). The preparation may comprise a solid, liquid, gel and combinations thereof and can include one or more pharmaceutical excipients. The preparation has a shape and material consistency to be contained in the swallowable capsule, delivered from the capsule into the lumen wall and degrade within the lumen wall to release the dose of therapeutic agent. Typically, this shape and material consistency are achieved by placing or forming the preparation into one or more embodiments of the tissue-penetrating members described herein. The preparation may also have a selectable surface area to volume ratio so as enhance or otherwise control the rate of degradation of the preparation in the wall of the small intestine or other body lumen. The dose of the drug or other therapeutic agent in the preparation can be titrated downward from that which would be required for conventional oral delivery methods so that potential side effects from the drug can be reduced.

In another aspect, the invention provides methods for the delivery of drugs and the therapeutic agents into the walls of a patient's gastric antrum and other regions of the GI tract using embodiments of the swallowable drug delivery devices. Such methods can be used for the delivery of therapeutically effective amounts of a variety of drugs and other therapeutic agents. These include a number of large molecule peptides and proteins that would otherwise require injection due to chemical breakdown in the stomach e.g., growth hormone, parathyroid hormone, insulin, interferons (for treatment of MS and other conditions) and other like compounds. Suitable drugs and other therapeutic agents that can be delivered by embodiments of invention include various antibodies (e.g., human epidermal growth factor receptor 2 (HER 2) antibodies), chemotherapeutic agents (e.g., interferon), insulin and related compounds for treating diabetes, glucagon like peptides (e.g., GLP-1, exenatide), parathyroid hormones, growth hormones (e.g., insulin-like growth factors (IGFs) and other growth factors), immune suppression agents (e.g., cyclosporines, cortisones, etc.), vaccines and anti-parasitic agents such as various anti-malarial agents. In specific embodiments, embodiments of the swallowable capsule can be used to delivery therapeutically effective amounts of the monoclonal antibody adalimumab for the treatment of various autoimmune related disorders such as rheumatoid arthritis. The dosage of this or particular therapeutic agent can be titrated for the patient's weight, age, condition or other parameter.

In various method embodiments of the present invention, embodiments of the swallowable drug delivery device including those using a drive and propellant can be used to deliver a plurality of drugs for the treatment of multiple conditions or for the treatment of a particular condition (e.g., a mixture of protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc., drugs can be absorbed through the intestinal wall at different rates, resulting in different pharmacokinetic distribution curves (e.g., plasma vs time curves). Embodiments of the present invention address this issue by injecting the desired drug mixtures at about the same time. This in turn, improves the pharmacokinetics and thus, the efficacy of the selected mixture of drugs.

Further details of these and other embodiments and aspects of the present invention are described more fully below, with reference to the attached drawing figures.

BRIEF DESCRIPTION OF THE DRAWINGS

FIG. 8A-1 to FIG. 8F-2 illustrate transit through and processing of a swallowable capsule in a patient's gastric antrum that results in injection of a therapeutic agent into an antral wall.

DETAILED DESCRIPTION

Embodiments of the present invention provide devices, systems, and methods for delivering drugs, substances, medications, and the like into an intestinal wall (e.g., small or large), stomach wall (e.g., antral wall) or other locations in the body. As used herein, the terms "therapeutic agent," "medicament," "medication," and "drug" are used interchangeably and refer to any medicinal preparation intended as a therapeutic, diagnostic, or other biologically active purpose in any form, which can include drugs or other therapeutic agents as well as one or more pharmaceutical excipients. Many embodiments of the present invention provide a swallowable device for delivering medication within the gastric antrum (GA), small intestine or other regions of the GI tract. Particular embodiments provide a swallowable device such as a capsule, for delivering medications into the wall of the small intestine or other location in the intestinal tract in response to a condition such as pH within a particular location or region in the GI tract. Other particular embodiments provide a swallowable device such as a capsule for delivering medications into the wall of the antrum or small intestine in response to pressure exerted on the capsule by contractions of the antrum.

Figure 1A:
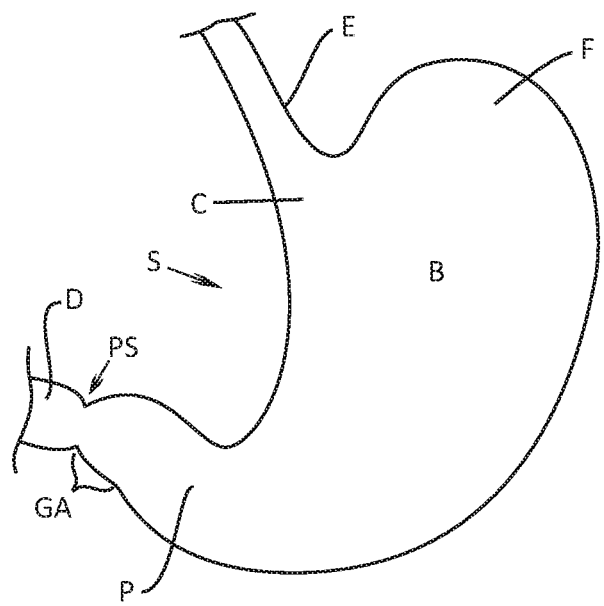
FIG. 1A illustrates regions of a patient's gastrointestinal (GI) tract, and in particular stomach, relevant to the devices and methods of the present invention.

The devices, systems, and methods of the present invention are particularly suited for delivering drugs to particular regions within a GI tract including for example portions of the stomach wall such as the antrum wall or portions of the small intestine such as the jejunum. Further, they are also suited to delivering drugs into the antrum wall or small intestinal even when partially digested food is present in the stomach. Referring now to FIG. 1A, after beginning the digestive process in the body of the stomach, the partially digested food enters the Fundus or body of the stomach then passes into the GA (also referred to as antrum A), where the devices and methods of the present invention will preferably deliver a therapeutic agent into a wall of the antrum. After delivering the therapeutic agent, the devices will pass through the pyloric sphincter PS and into the duodenum D from where the intact, partially degraded, or fully degraded device passes through the large intestines and be excreted from the body.

Figure 1B:
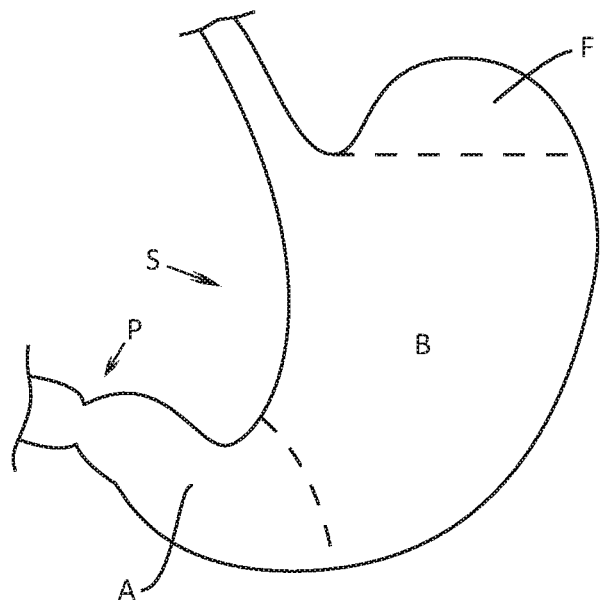
FIG. 1B illustrates the anatomical regions of a patient's stomach.
Figure 1C:
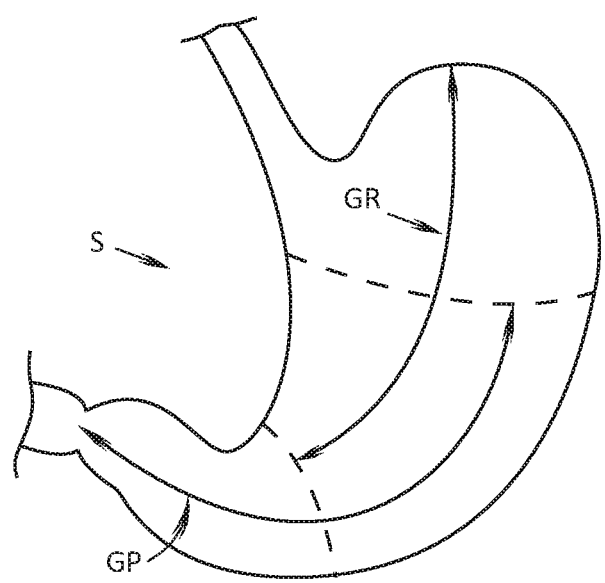
FIG. 1C illustrates the functional regions of a patient's stomach.

As many embodiments of the present invention contemplate delivery of drugs and other therapeutic agents into walls of the GI tract including walls of the gastric antrum, a brief invention will now be provided on the anatomy and function of the GI tract including the stomach. As shown in FIG. 1A, the GI tract begins with the esophagus E and enters the stomach S at the cardia C. Food thus enters the stomach through the esophagus after passing through the cardia. As shown in FIG. 1B, the major anatomic regions of the stomach include the fundus F, the corpus or body B, the antrum (A) and pylorus P. While the wall of the fundus is thin, the wall of the antrum is much thicker (due to a muscular layer), easily allowing for delivery of an embodiment of solid drug dose described herein. However, the functional regions of the stomach do not correspond to the anatomic regions. As shown in FIG. 1C, functionally, the stomach can be divided into the gastric reservoir GR and the gastric pump GP. The gastric reservoir includes the fundus F and corpus or body B. The gastric pump is represented by the area at which peristaltic waves occur: it includes the distal part of the corpus and the antrum. Due to different properties of the smooth muscle cells, the gastric reservoir is characterized by tonic activity and the gastric pump by phasic activity known as peristaltic waves. The main feature of the gastric pump is the peristaltic wave. It originates at the proximal stomach and propagates to the pylorus. The peristaltic waves are based on electrical waves originating in the gastric wall. In the wall of both the stomach and small intestine, there is a network of interstitial cells—called interstitial cells of Cajal (ICC). These interstitial cells produce electrical pacesetter potentials due to oscillations in their membrane potential. The pacesetter potential of the ICCs drives electrical events in the smooth muscle cells where they are reflected by slow waves. The frequency of the pacesetter potentials and the resulting peristaltic contractions occur approximately three times a minute or about 20 seconds. The pacesetter potentials determine the maximal frequency and the propagation velocity of the peristaltic wave. In the region of the gastric corpus the peristaltic waves are shallow; they represent—as mentioned above—the pump of the gastric reservoir. When the peristaltic wave reaches the antrum (A), the circular constriction of the antrum becomes deeper such that the antrum develops into a tubular shape in which force is applied to the contents of the antrum. The emptying mechanism of the antral pump can be divided into three phases: 1) a phase of propulsion, 2) a phase of emptying and mixing, and 3) a phase of retropulsion and grinding. When the peristaltic wave moves over the proximal antrum the previously contracting terminal antrum relaxes. As such chyme and other stomach contents are propelled into the distal (or terminal) antrum (phase of propulsion). When the peristaltic wave moves over the middle of the antrum, the pylorus opens and duodenal contractions are inhibited; thus, small amounts of gastric chyme are delivered across the pylorus into the duodenum. During this phase of emptying and mixing, the peristaltic waves are relatively far away from the pylorus, i.e. the gastric chyme is not forced into the duodenum by pressure but is swept into the small intestine by the peristaltic wave. This mechanism of the antral pump is associated with a sieving effect. In particular, the shape of the antrum becomes tubular allowing for flow of liquid and small particles from the pylorus into the duodenum whereas more solid matter including embodiments of the of swallowable capsule 10 are retained in the antrum being blocked by the relatively small opening of the pylorus. When so retained during this this phase of antral contractions, the forces of the contracting antrum are applied to the surface of the capsule where they may be sensed using a pressure or other sensor 12 described below.

Figure 2:
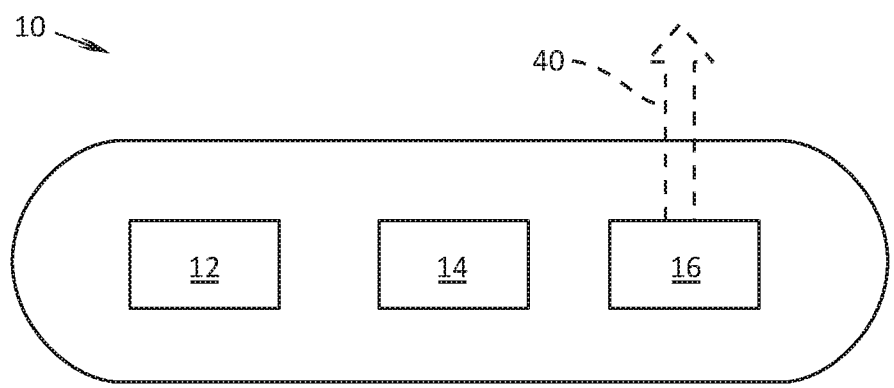
FIG. 2 illustrates the principal components of a swallowable drug delivery device constructed in accordance with the principles of the present invention.

A swallowable capsule 10 constructed in accordance with the principles of the present invention will typically include a pressure or other proximity sensor 12, a driver 14, and a drug dosage 16 to be delivered, as shown in FIG. 2. The nature of these specific components can vary widely depending, inter alia, on the mode of drug delivery and the target drug delivery region within the GI tract. For example, the pressure or other proximity sensor 12 may be mechanical, electrical, or combinations thereof. The sensor 12 will typically be able to sense force/pressure applied externally to the swallowable capsule 10, and in particular will be able to sense when pressure is being applied to the exterior of the capsule by contractions of the antrum. It will be appreciated that the pressure applied by the antrum is unique within the GI tract and sensing of pressures exceeding a minimum threshold value may be relied upon to indicate that the swallowable capsule 10 has reached the interior of the antrum.

The driver 14 may also have any one of a variety of forms. The drivers may rely on mechanical, electrical, chemical or other stored energy in order to initiate release of the therapeutic agent 40 from the capsule as indicated by the broken arrow shown in FIG. 2. The driver 14 will be coupled to the pressure or other proximity sensor 12 so that the driver will be actuated in response to the pressure sensor sensing a pressure above the predetermined threshold value, indicating that the swallowable capsule 10 has reached the interior of the patient's antrum. In some instances, the sensor and the driver may be configured to convert the pressure applied by contractions of the gastric antrum into a force that drives the drug into the antral wall.

Figure 3:
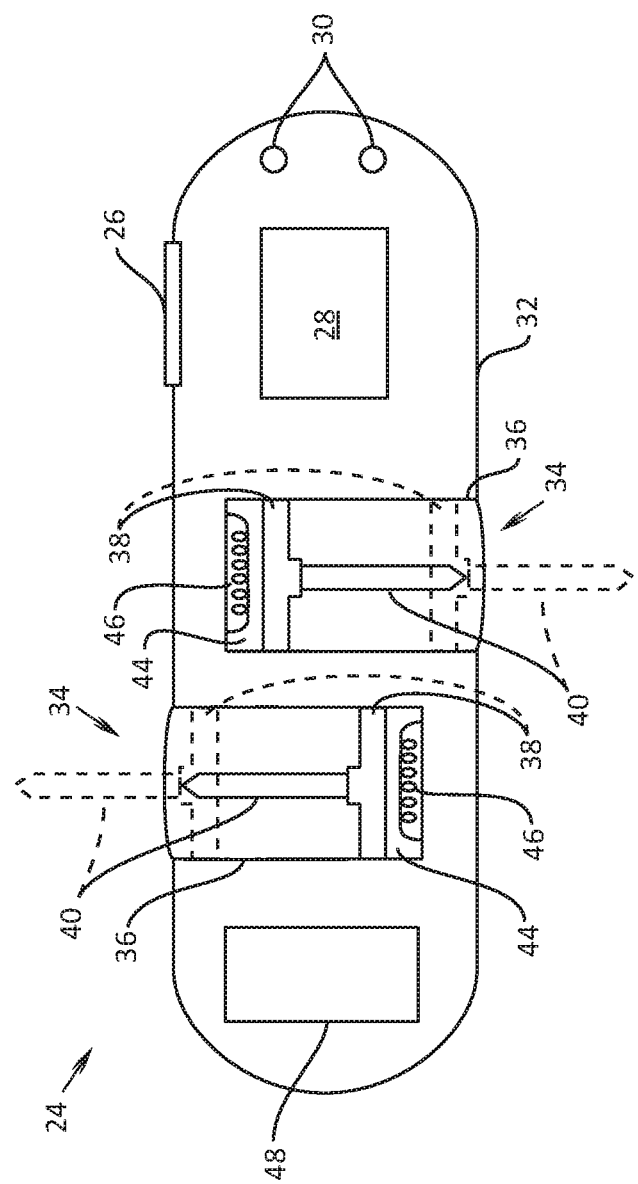
FIG. 3 illustrates the principal components of a particular embodiment of a swallowable drug delivery device constructed in accordance with the principles of the present invention.

Referring now to FIG. 3, a particular embodiment of a swallowable capsule 24 having the operative components of the present invention is shown in more detail. A solid state pressure sensor 26, such as a solid state piezoelectric element, is typically mounted in an external wall of the capsule. According to specific embodiments, the pressure sensor 26 or other proximity sensor 12 may positioned in close proximity (1 to 5 mm) to where the solid drug dosage 40 (e.g., a tissue penetrating member TPM) exits the capsule 24 (e.g., where cylinders 36 are positioned in the capsule) so that there can be increased assurance that the antrum wall is indeed in contact with the capsule surface when driver 14 is triggered to eject that solid drug dosage into the antrum wall. In this way, there is increased reliability that the solid drug dosage 40 is delivered into the antral wall or other desired location in the stomach, or other portion of the GI Tract. The pressure sensor 26 is connected to a control module 28 (also referred to herein in as a controller 28) in the interior of the capsule. The control module 28 will typically include microprocessor and associated application software executable on the process to control all (or a portion of the) operations of the swallowable capsule 24, as described in more detail below. In an alternative embodiment, control module 28 may be or include an analogue device as well. In some embodiments, the swallowable capsule 24 will also have fluid or other sensors 30 to confirm when the swallowable has been swallowed and is in the stomach so as turn on capsule power to begin sensing pressure by pressure sensor. According to one or more embodiments, fluid sensors 30 may correspond to electrodes disposed on the capsule surface or other location on the capsule that sense conductive bridging between the electrodes by digestive fluids in the stomach, to confirm when the capsule has entered the stomach. In use, fluid sensors 30 serve to conserve power of the battery or other electrical power source 48 so that the capsule only begins to expend power to sense applied pressure to the capsule by surface after the capsule has been swallowed.

The swallowable capsule 24 is surrounded by capsule wall 32 enclosing an interior that holds a pair of drug delivery modules 34. Each drug delivery module 34 includes a cylinder 36 having a reciprocating piston 38 therein. The piston 38 is initially retracted, as shown in FIG. 3, having a space adjacent a bottom of the associated cylinder 36. The space may be filled with a chemical propellant 44 and may have a coil or other igniter 46 therein. In this way, the control module 28 may electrically ignite the propellant 44, so as to drive solid dosage drugs 40 in the directions shown in broken line in FIG. 3 by the force generated from the ignited propellant. According to one or more embodiments the chemical propellant may correspond to a flammable membrane such as nitrocellulose or other nitrated polymer that may be formed into a layer or otherwise disposed into a well that is positioned at the bottom of cylinder 36. When positioned within a well, the propellant 44 and well may be structured so as to provide a directional energy delivery upon ignition. In specific embodiments, where the propellant 44 comprises a nitrocellulose layer or other shape, the mass of the nitrocellulose layer (or other shape) may be in a range from about 1 to 8 mg, more preferably, about 3 mg. Experimental studies with 3 mg of nitrocellulose resulted in a velocity of the tissue penetrating member 40 of around 30 meters per second. In alternative or additional embodiments, the nitrocellulose or other propellant 44 may be embedded or otherwise incorporated into a bottom portion (e.g. non tissue penetrating portion) of the shaft of solid drug dosage 40. The igniter 46, including an igniter wire or wire coil ignitor 120/220 (FIG. 4, FIG. 5) may adhere or otherwise be operably coupled to or positioned at the bottom portion of dosage 40 (or reciprocating piston 38) so as to ignite the nitrocellulose or other propellant 44 in a manner similar to as described herein.

In some embodiments, igniter 46 may comprise a conductive wire that is coated with a compound that acts as an accelerant to combustion in combination with ignition of propellant 44. This would have the effect of forming a two-stage combustion, wherein the first stage includes igniting the accelerant coating, and the second stage includes igniting the propellant 44. Exemplary compounds for the accelerant coating include but are not limited to: Conductive Hot Shot Pyrogen mix, H-3 Pyrogen mix, and QuickDip, all manufactured by Quickburst, Trinity TX Such accelerant coating compound may also be selected for adhesion to the igniter wire 46. In one embodiment, the ignitor coil may even be composed of the accelerant compound itself (i.e. not layered on a wire). For example, the Conductive Hot Shot Pyrogen compound is conductive and may be used as both the conductive ignitor wire and ignition accelerant.

The swallowable capsule 24 will typically also carry a chemical storage battery (e.g., a lithium battery) or other electrical power source 48 in order to power the control module 28, igniters 46, and other components of the capsule 24. In some embodiments, electrical power source 48 may correspond to a capacitor. In particular embodiments where the propellant 44 corresponds to ignitable material such as nitrocellulose or other ignitable chemical propellant, which is ignited by ignitor(s), the ignitor 48 may have its own dedicated power source (not shown) that will typically correspond to a capacitor configured to provide sufficient current and voltage to ignite ignitor 46.

The solid dosage drugs 40 are typically self-penetrating, often having sharpened, honed, or other tissue-penetrating tips. Details of such solid dosage forms may be provided in additional detail below.

Figure 4:
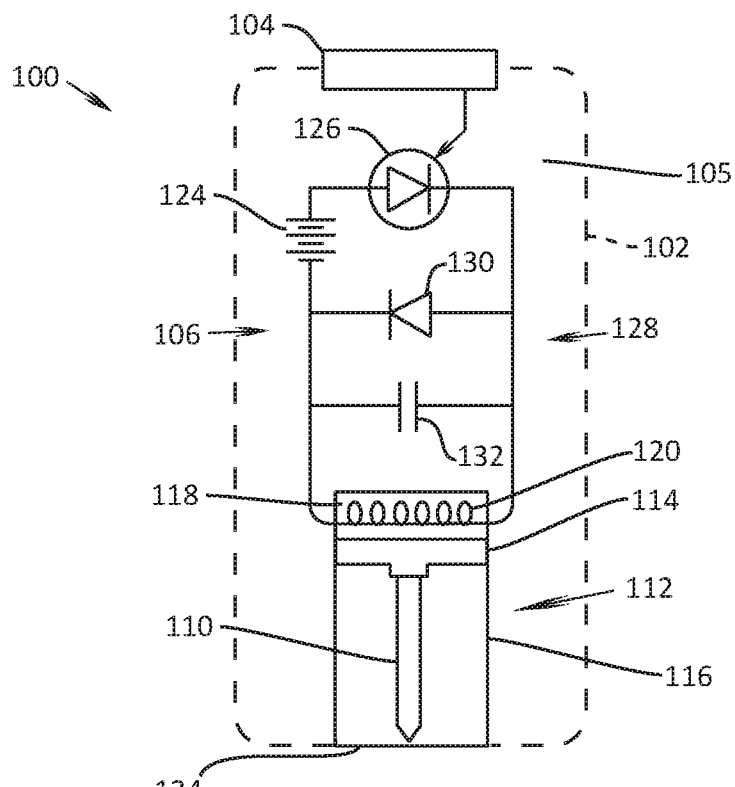
FIG. 4 illustrates the principal components of a further embodiment of a swallowable drug delivery device constructed in accordance with the principles of the present invention and including an electronic sensor and power boost circuit.

Referring now to FIG. 4, according to one or more embodiments, a swallowable capsule 100 comprises a capsule wall or shell 102 sized and configured to permit swallowing so that the capsule will pass through a patient's esophagus into the stomach, through the pylorus, and into the small intestines and/or subsequently into the large intestine. Adaptions in size and shape may be made for pediatric, neonatal and veterinarian applications. Depending on the specific structure of the capsule, its internal components and the materials of both, the capsule may be fully degraded within the patient's intestines or may be excreted from the intestines by normal digestive processes. Typically, the capsule wall 102 will be formed from a biodegradable material that will persist sufficiently long so that the capsule will pass through the stomach into the intestines and eventually be digested within the intestines. The internal components of the swallowable capsule 100, in contrast, may comprise non-toxic metals, ceramics, plastics, or other materials that are not digested within the intestines and that will be excreted from the intestines in the course of normal digestion. Such non-degradable components, however, will be formed to have sizes, geometries, and other characteristics, which make them benign to the patient as they are being excreted.

According to one or more embodiments, the swallowable capsule 100 includes one or more sensors 104 located in the capsule wall 102 so that it has an exterior surface exposed outwardly from the capsule and an interior surface in communication with an interior region 105 of the capsule. A driver circuit 106 is also located in the interior 105 of the swallowable capsule 100 and is configured to receive a signal from the sensor(s) 104 in order to generate a current to trigger release of therapeutic agent from the capsule. In particular, the driver circuit 106 is operatively coupled to a drug delivery module 112 that is configured to advance and release a solid drug dosage 110, typically in the form of a tissue-penetrating member or TPM as described elsewhere herein. The drug delivery module 112 typically includes a piston 114 received in the interior of a cylinder 116 and disposed to reciprocate within cylinder 116. The solid drug dosage 110 is located on a surface of the piston 114 that is selectively driven in a direction toward the capsule wall 102 so that the dosage 110 may be delivered through the wall and into an adjacent intestinal wall or other lumen wall of the GI-tract. The piston 114 is driven by the ignition of a combustible propellant 118 disposed at an end of the cylinder 116 opposite to that of the direction in which the piston is to be driven.

According to one or more embodiments, the driver circuit 106 is configured to generate a current sufficient to ignite the combustible propellant 118, for example using a filament or other wire ignitor. In particular embodiments the filament may comprise tungsten, Nichrome or an alloy thereof. For example, the driver circuit 106 may include a battery 124, a trigger 126, typically in the form of a silicon-controlled rectifier (or SCR), and a booster/converter circuit 128 including a transistor 130 and a capacitor 132. The trigger 126 receives a signal from the sensor 104 when the requisite condition exists for delivering the solid drug dosage 110. Once the condition is sensed by the sensor 104, a low voltage signal is sent to the trigger, which in turn opens the circuit to deliver current from the battery 124 to the capacitor 132. The combination of transistor 130 and capacitor 132 are arranged and configured to act as a current booster that will further trigger delivery of the current to a wire coil ignitor 120 embedded or otherwise in contact with the combustible propellant 118.

Combustion of the combustible propellant 118 causes the release of energy and expansion of gases sufficient to drive the piston 114 in a direction toward the capsule wall. The force with which the piston 114 is driven will be sufficient to drive the solid drug dosage 110 through the wall 102, typically through a frangible barrier 134 formed in a region of the wall that will be adjacent to a target portion of the patient's gastrointestinal wall (e.g. the antral wall, small intestine wall, etc.).

Figure 5:
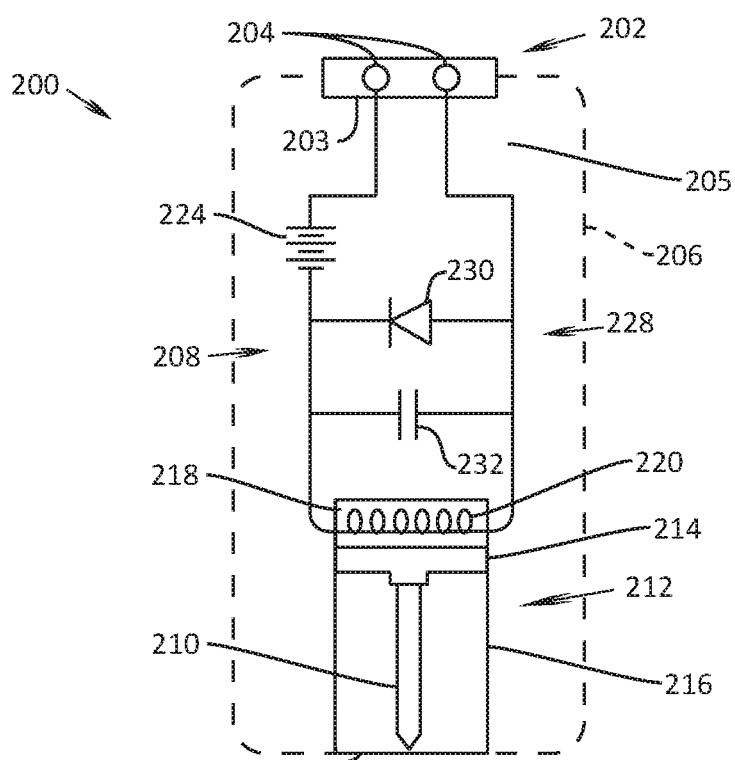
FIG. 5 illustrates the principal components of another embodiment of a swallowable drug delivery device constructed in accordance with the principles of the present invention and including a pH sensitive switch and power boost circuit.

An alternative embodiment of a swallowable capsule 200 is illustrated in FIG. 5. Instead of a sensor 104 as in the embodiment of FIG. 4, in this embodiment the swallowable capsule 200 includes a trigger switch 202 formed in a wall 206 of the capsule. For example, the trigger switch 202 may include a biodegradable body 203 having a pair of electrical contacts 204 embedded therein. When the swallowable capsule initially enters the patient's GI tract, the biodegradable body 203 will initially insulate the contacts from the contents of the GI tract, including at least a portion of the stomach. Over time, the biodegradable body 203 will degrade to expose the electrical contacts 204 such that the electrically conductive contents of the GI tract (e.g. stomach acid, bile, chime, etc.) will provide an electrically conductive pathway between the pair of contracts. In this way, a driver circuit 208 may be closed in order to initiate delivery of the solid dosage drug 210 in a manner similar to that described in the previous embodiment.

For example, according to one embodiment the biodegradable body 203 may be formed from a pH-sensitive material, such as a poly(meth)acrylate (PMA) that is soluble in digestive fluids including digestive fluids having a selected pH such as that in the stomach or the small intestine. Commercially available soluble PMA polymers are available under the trade name Eudragit® polymer from Evonik Nutrition & Care GmbH, Essen, Germany.

The remaining structure of the swallowable capsule 200 may be similar to that of the swallowable capsule 100. In particular, a drug delivery module 212 may be located within interior region 205 of capsule wall 206 and include a piston 214 disposed to reciprocate within a cylinder 216. A combustible propellant 218 is located at one end of the cylinder 216 and an igniter wire 220 is embedded in the combustible propellant.

The driver circuit 208 includes a battery 224, and a booster/converter circuit 228 including a transistor 230 and a capacitor 232. Charging of the capacitor 232 is initiated at the time the electrical contacts 204 are electrically coupled by exposure to the electrically conducted contents of the patient's GI tract. Initiation of the driver circuit 208, in turn, delivers current to the embedded ignitor wires 220 within the combustible propellant 218 in order to initiate combustion and drive the solid drug dosage 210 through frangible barrier 234 as described with the previous embodiment.

In FIG. 4 and FIG. 5, the location of the drug delivery module 112/212 is disposed at ends of the capsule wall 102/206, such that the solid drug dosage 110/210 is delivered substantially along the long or longitudinal axis of the capsule 102/206. However, it is appreciated that the illustrations in FIG. 4 and FIG. 5 are primarily for schematic purposes, and that the orientation and location of the drug delivery module 112/212 may be perpendicular to the longitudinal axis of the capsule 102/206 (i.e. radially oriented with respect to the circumference of the capsule wall 102/206), as detailed above with respect to the drug delivery modules 34 shown in FIG. 3.

Additional or alternative embodiments contemplate mechanical ignitors that may include a trigger or latch that degrades in response to a condition in the GI tract, including, for example, exposure to fluids in the GI tract, in particular exposure to fluids having a particular pH such as that found in the small intestine (e.g., between 6 to 7.4). In particular embodiments, the ignitor may include a micro-machined or mems-based pre-tensioned spring device (not shown) having one or more frictionally reactive portions that generate sparks or flames upon movable contact with another surface. The ignitor is held in the pre-tensioned state by the degradable latch and when the latch degrades, the frictionally reactive portions contact each other, another surface of the ignitor or an external surface thereby generating a spark or flame that ignites the nitrocellulose or other propellant. The reactive portions may include materials found in match heads or high carbon steel for one reactive portion and flint or high silica material for an opposing portion.

According to one embodiment of such an ignitor, the ignitor may have a tweezer like shape that is held in the contracted by the degradable latch. The arms of the tweezer are slightly offset from each including the reactive portions contained on the tweezer arms such that they rub past each other when the latch is released and generate the spark that ignites the propellant. In an alternative embodiment, the tweezer by have be in an over extended expanded shape such that the when the latch is degraded the arms spring together resulting in forceful contact of the reactive portions and generation of the spark or flame. In various embodiments, the mechanical ignitor may be fabricated from various biocompatible and/biodegradable polymers known in the art including for example, PEO (polyethylene oxide), PLGA, silicone and other elastomers known in the art. They may also be produced using one or more of mems, photolithography, 3-D printing and various micro-machining methods known in the art.

Figure 6:
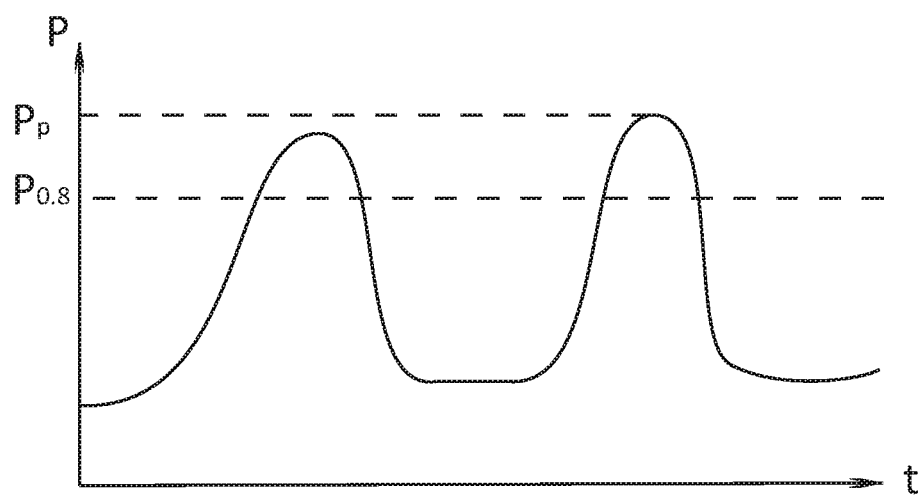
FIG. 6 is a graph illustrating a typical pressure profile in a patient's gastric antrum during normal digestive processing of food.

Referring now to FIG. 6, according to one or more embodiments the pressure sensor 26 and control module 28 of the swallowable capsule 24 may be configured and programmed to sense changes in the external pressure/force applied to the capsule wall by peristalsis of the antral wall known as antral peristalsis. Antral peristalsis typically comprises a series of pressure waves, as shown in FIG. 6, having a peak pressure $P_p$. Particular peak pressure values may be determined for a patient population and/or for a particular patient, and a pressure value may be selected that is less than the peak pressure $P_p$ at which to initiate therapeutic preparation delivery from the swallowable capsule 24. For example, the trigger pressure may be 80% of the peak pressure value, which is detailed as $P_{0.8}$ in FIG. 6. It is appreciated that other trigger pressure values may also be selected (e.g., 70%, 85%, 90%, etc. of peak pressure $P_p$). As described according to some embodiments, peak pressure $P_p$ may be determined by configuring the capsule to be retained in the antrum for several peristaltic contractions of the antrum and configuring the controller 28 and/or control module to record applied antral pressures through several cycles of peristaltic contractions, and then calculate average peak pressure as well as other information related to antral peristaltic contractions, including but not limited to average frequency and period of contractions.

Figure 7:
FIG. 7 illustrates a test capsule for measuring pressure in a patient's GI tract.

According to some embodiments, the patient may first swallow a test capsule or capsule mimic 24' (FIG. 7) that does not necessarily contain a driver 14 and therapeutic agent 40, but rather whose primary function is to record the applied pressure to the capsule 24' through a number of antral peristaltic contractions and then calculate and transmit to an external device various data related to those contractions, including one or more of average peak peristaltic pressure, frequency and period of contraction and the like. A pressure sensor 25 may be coupled to an outer surface of test capsule 24' to capture such data. Internal circuitry (not shown) may also be provided for recording and/or transmitting the observed pressure data as test capsule 24' travels through the GI tract. The acquired data/information may then be input into the swallowable capsule 24, for example from an external device (not shown) to controller 28 (e.g., processor or other control module) of the capsule 24, and then be utilized to modify trigger timing or otherwise control the release of therapeutic agent into antral wall. In these and related embodiments, the control module 28 may include or otherwise by operatively coupled to memory means (e.g., ram, dram, volatile memory, etc.) for storing acquired data and/or application software executable on the controller in the operation of the device, as well as transmission means such as an RF, Wifi, other transmission device known in the art. In particular embodiments, the transmission/transceiver device may be configured to use a Bluetooth communications protocol so as to communicate with an external device such as cell phone, tablet and the like.

Referring now to FIG. 8A-1 through FIG. 8F-2, the delivery of a swallowable capsule 10 (or any of swallowable capsules 24, 100, and 200 detailed above) to an antral wall (AW) in accordance with the principles of the present invention will be described. Initially, the gastric antrum (GA) is empty while the AW is undergoing peristaltic contractions and thus constrictions, as shown in FIG. 8B-1 and FIG. 8B-2. The patient then ingests a swallowable capsule 10, and the capsule eventually approaches the GA as shown in FIG. 8C-1 and FIG. 8C-2. As the swallowable capsule 10 enters the GA, the gastric walls will constrict over its exterior, as shown FIG. 8D-1 and FIG. 8D-2. As a result of the pressure exerted by the AW, the sensor 26 of the capsule 10 then senses the elevated pressure/force, and then releases the solid dosage forms 40 through the wall of the capsule and into the AW, as shown in FIG. 8D-1 and FIG. 8D-2.

In particular implementations, the control module 28 or other circuitry can be configured to measure and store the pressure/force vs time curves from several peristaltic contractions of the antrum wall in order to develop a database of pressure/force curves of antral contractions for an individual patient particularly occurring during one or more phases the antral pump described above. Further as described below, various information including parameters such as peak peristaltic pressure/force (or a selected of peak pressure e.g. 80%) applied to the capsule and frequency and/or period of peristaltic contractions of the antrum may be derived from the pressure/force curves by the control module or logic means. In various embodiments, one or a combination of these or other parameters may be used by control module 28 to trigger the release of solid dosage 40 into the antrum wall for example using ignitable propellant described herein. In a particular approach, the control module 28 can be configured to use both a percentage of peak contractile pressure and period of contraction to trigger release of solid dosage 40. In using one or more of these approaches, the capsule 10 is better able to sense when a peristaltic wave/contraction occurs of the antrum that results in a desired amount of contraction and/or contact of the antrum on the capsule 10. In this way, the reliability of the delivery of the solid form dosage 40 into the antral wall (or other portion of the stomach or GI tract) is significantly improved.

In various embodiments, the capsule 24 may be desirably sized and shaped or otherwise configured to remain in the antrum during several peristaltic contractive phases of the antral pump so that it may sense and record multiple peristaltic contractions of the antrum so as derive information of the antral contractions unique to a particular patient, including average peak antral peristaltic pressure applied to the capsule as well as the frequency and/or period of antral peristaltic contractions. This can be accomplished through various approaches. For example, according to one approach, the diameter of capsule 24 can be sized such that it is somewhat larger than that of the only the partially opened pyloric valve or sphincter PS. In additional or alternative embodiments, the capsule can be configured to remain in the antrum during peristaltic contractions that might otherwise force it out of the antrum through the use of various surface coatings or surface features that ensure that the capsule 24 is gripped by or held against the antrum during contraction. The coatings may include pressure activated bio-adhesive coatings, including pressure activated bio-adhesives having weak adhesive forces known in the art. Such surface features may include various texturized surfaces known in the art, including knurled surfaces that increase the coefficient of friction between the surface of antrum and the capsule surface when the capsule is gripped by the antrum, thus increasing the amount of force required to force the capsule distally out of the antrum.

The antral wall will continue to undergo peristalsis, eventually releasing the swallowable capsule 10 as shown in FIG. 8E-1 and FIG. 8E-2. The capsule 10, if it hasn't completely degraded, will then pass through the pyloric sphincter (PS) and into the Duodenum D, as shown in FIG. 8F-1 and FIG. 8F-2. After passing through the pyloric sphincter PS and duodenum D, the capsule 10 will then eventually be excreted from the patient.

Referring back to FIG. 3, in various embodiments, swallowable capsule 24 including tissue-penetrating member 40 can be configured for the delivery of liquid, semi-liquid or solid forms of medication, or combinations of all three. Whatever the form, the medication desirably has a material consistency allowing the medication to be advanced out of swallowable capsule 24, into a target location on the antral or other GI wall (e.g., the small intestine) and then degrade within the wall to release the drug or other therapeutic agent. The material consistency of the medication may be formulated to enhance/optimize one or more of the hardness, porosity and solubility of the preparation (in body fluids). The material and dimensions of the tissue-penetrating member or other drug dosage 40 may also be optimized for the particular target location in the GI tract. For example, for delivery into the antral wall longer tissue-penetrating members may be used with greater degree of hardness in order to penetrate the more muscular portions of the antrum wall. The material consistency can be achieved by selection and use of one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art.

Swallowable capsule 24 is sized to be swallowed and pass through the GI tract at least to the antrum. However, in particular embodiments the diameter of the capsule can be sized such that it is retrained in the antrum when the pyloric valve is only partially opened. The size can also be adjusted depending upon the amount of drug to be delivered as well as the patient's weight and adult vs. pediatric applications. In additional or alternative approaches, the capsule may also include surface coatings and features described herein to help retain the capsule in the antrum when pyloric valve is only partially opened. Typically, the capsule will have a tubular shape with curved ends similar to a vitamin. In these and related embodiments, capsule lengths can be in the range of 0.5 to 2 inches and diameters in the range of 0.1 to 0.5 inches, with other dimensions contemplated. The swallowable capsule 24 includes a capsule wall 32, having an exterior surface and an interior surface defining an interior space or volume. In some embodiments, the capsule wall can include one or more apertures sized for the outward advancement of tissue-penetrating members 40.

The swallowable capsule 24 will typically, but not necessarily, be fabricated from a biodegradable material, such as a gelatin as known in the pharmaceutical arts, and may include an enteric coatings configured to protect the capsule from degradation in the stomach and antrum (due to acids etc.), and then subsequently degrade in the in higher pH's found in the small intestine or other area of the intestinal tract. In various embodiments, the swallowable capsule 24 can be formed from multiple portions or segments (e.g. two halves) one or more of which may be biodegradable.

As is discussed above, one or more portions of capsule 24 can be fabricated from various biocompatible polymers known in the art, including various biodegradable polymers that in a preferred embodiment can comprise cellulose, gelatin materials, PLGA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

Use of biodegradable materials for swallowable capsule 24, including biodegradable enteric materials allows the capsule to degrade in whole or part to facilitate passage through the GI system before, during or after drug delivery. As is described in further detail herein, in various embodiments, swallowable capsule 24 can include seams 22 of bio-degradable material so as to controllably degrade into smaller pieces 23 that are more easily passed through the intestinal tract.

In various embodiments, swallowable capsule 24 can include various radio-opaque, echogenic or other materials for location of the device using one or more medical imaging modalities such as fluoroscopy, ultrasound, MRI, etc. In specific embodiments, all or a portion of the capsule can include radio-opaque/echogenic. Suitable materials for radio-opaque markers include barium sulfate, compounds, titanium dioxide and compounds thereof. In use, such materials allow for the location of swallowable capsule 24 in the GI tract, as well as its state of deployment (e.g., a distinctive marker can be positioned on each end and optionally elsewhere on the wall 32) allowing for visual confirmation that the swallowable capsule 24 has properly aligned in the antrum prior to release of the therapeutic agent. They can also be used allow for the determination of transit times of the device through the GI tract. Such information can be used to titrate dosages of drug for a particular patient, as well as provide information on when they should take a particular drug after an event such as ingestion of a meal, e.g. in the case of insulin taken for treatment of diabetes.

Tissue-penetrating members 40 can be fabricated from various drugs and other therapeutic agents, one or more pharmaceutical excipients (e.g., disintegrants, stabilizers, etc.), and one or more biodegradable materials (e.g. PEO), which may be used to form the main structural component of a TPM including a shaft having a tip as discussed below and described in detail in U.S. Pat. Nos. 9,757,548; 8,562, 589; 8,809,269; 8,969,293; 8,809,271; 8,980,822; 9,861, 683; 9,259,386; 9,284,367; 9,149,617; 8,734,429; 9,283, 179; 8,764,733; 9,402,806; 9,629,799; 9,415,004; 9,402, 807; 8,846,040; 10,098,931; and 10,220,003; and U.S. application Ser. Nos. 15/144,733; 15/150,379; 15/260,260; 15/928,606; 16/183,573; and provisional application No. 62/786,831, having common inventorship with the present application, the full disclosures of which are incorporated herein by reference for all purposes.

Specific materials can be chosen to confer desired structural and material properties to the penetrating member (for example, column strength for insertion into the stomach or intestinal wall, or porosity and hydrophilicity for controlling disintegration of the penetrating member and thus the release of drug). In many embodiments, the penetrating member 40 can be formed to have a shaft and a needle tip or other pointed tip so as to readily penetrate tissue of the antrum or other intestinal wall, as shown for example in FIG. 8D-1 and FIG. 8D-2. In exemplary embodiments, the tip has a trocar and may comprise various degradable materials (within the body of the tip or as a coating), such as sucrose, maltose or other sugar increase the hardness and tissue-penetrating properties of the tip. Once placed in the intestinal wall, the penetrating member 40 is degraded by the interstitial fluids within the wall tissue so that the drug or other therapeutic agent dissolves in those fluids and is absorbed into the blood stream. One or more of the size, shape, and chemical composition of tissue-penetrating member 40 can be selected to allow for dissolution and absorption of an incorporated drug in a matter of seconds, minutes or even hours. Rates of dissolution can be controlled through the use of various disintegrants known in the pharmaceutical arts. Examples of disintegrants include, but are not limited to, various starches such as sodium starch glycolate and various cross linked polymers such as carboxymethyl cellulose. The choice of disintegrants can be specifically adjusted for the environment within the wall of the small intestine e.g., blood flow, average number of peristaltic contractions, etc.

Tissue-penetrating member 40 may also typically include one or more tissue retaining features, such as a barb or hook to retain the penetrating member within the tissue of the antral or other region of the intestinal wall after advancement. Retaining features can be arranged in various patterns to enhance tissue retention such as two or more barbs symmetrically or otherwise distributed around and along member shaft. Additionally, in many embodiments, penetrating member may also include a recess or other mating feature for attachment to a coupling component on delivery mechanism. Such features are described in more detail in U.S. Pat. No. 8,734,429, which has previously been incorporated herein by reference.

Tissue-penetrating member 40 is desirably configured to be detachably coupled to piston 38 so that after advancement of the tissue-penetrating member 40 into the antral wall, the tissue-penetrating member detaches from the piston. Detachability can be implemented by a variety of means including: i) the snugness or fit between an opening in the piston; ii) the configuration and placement of tissue retaining features on the tissue-penetrating member 40 that anchor the tissue-penetrating member is tissue to promote detachment from the piston; and iii) the depth of penetration of the tissue-penetrating member into the intestinal wall. Using one or more of these factors, tissue-penetrating member 40 may be configured to detach as the piston is retracted or otherwise pulls back away from the antral wall and/or the forces exerted on swallowable capsule 24 by a peristaltic or other contractions of the antrum.

As described above, in various embodiments, tissue-penetrating member 40 can be fabricated from a number of drugs and other therapeutic agents. Also, according to one or more embodiments, the tissue-penetrating member may be fabricated entirely from drug or may have other constituent components as well, e.g., various pharmaceutical excipients (e.g., binders, preservatives, disintegrants, etc.), polymers conferring desired mechanical properties, etc. Further, in various embodiments one or more tissue-penetrating members 40 can carry the same or a different drug (or other therapeutic agent) from other tissue-penetrating members. The former configuration allows the delivery of greater amounts of a particular drug, while the later allows two or more different drugs to be delivered into the antral wall at about the same time to facilitate drug treatment regimens requiring substantial concurrent delivery of multiple drugs.

Typically, the drug or other therapeutic agent carried by the tissue-penetrating member 40 will be mixed in with a biodegradable material to form tissue-penetrating member 40. The biodegradable material may include one or more biodegradable polymers such as PEO (polyethylene oxide), PLGA, cellulose, as well as sugars such as maltose or other biodegradable material described herein or known in the art. In such embodiments, the penetrating member 40 may comprise a substantially heterogeneous mixture of drug and biodegradable material. Alternatively, the tissue-penetrating member 40 may include a portion formed substantially from biodegradable material and a separate section that is formed from or contains drug. Shaped sections may be pre-formed as a separate section that is then inserted into a cavity in tissue-penetrating member 40 to allow for a modular fabrication. Alternatively, drug preparation may be introduced into to cavity(ies) in the tissue-penetrating member 40, e.g. being combined as a powder, liquid, or gel that is poured or injected into a cavity, well, hollow interior, or other receptacle in the tissue-penetrating member 40. Shaped section 42s may be formed of drug by itself or a drug preparation containing drug and one or more binders, preservatives, disintegrates and other excipients.

In various embodiments, the weight of tissue-penetrating member 40 can range between about 10 to 15 mg, with larger and smaller weights contemplated. For embodiments of tissue-penetrating member 40 fabricated from maltose, the weight can range from about 11 to 14 mg, while for PEO the weight of the tissue-penetrating member can in be in the range of 10 to 15 mg. In various embodiments, depending upon the drug and the desired delivered dose, the weight percentage of drug in member 40 can range from about 0.1 to about 15%. The weight percentage of drug in member 40 can be adjusted depending upon the desired dose as well as to provide for structural and stoichiometric stability to the drug and also to achieve a desired elution profile of the drug. Table 1 lists the dose and weight percentage range for a number of drugs that may be delivered by tissue-penetrating member 40.

TABLE 1

| Drug | Dose Via Capsule** | % Weight of Drug in the needle |
| --- | --- | --- |
| Insulin | 5-30 Units | 2-15% |
| Exenatide | 10 ug | <1% |
| Liraglutide | 0.6 mg | 3-6% |
| Pramlintide | 15-120 ug | 0.1-1% |
| Growth Hormone | 0.2-1 mg | 2-10% |
| Somatostatin | 50-600 ug | 0.3-8% |
| GnRH and Analogs | 0.3-1.5 mg | 2-15% |
| Vasopressin | 2-10 units | <1% |
| PTH/Teriparatide | 20 ug | 1-2% |
| Interferons and analogs | | |
| 1. For Multiple Sclerosis | 0.03-0.25 mg | 0.1-3% |
| 2. For Hep B and HepC | 6-20 ug | 0.05-0.2% |
| Adalimumab | 2-4 mg /day | 8-12% |
| Infliximab | 5 mg/day | 8-12% |
| Etanercept | 3 mg/day | 8-12% |
| Natalizumab | 3 mg/day | 8-12% |

Tissue-penetrating member 40 may be fabricated using one or more polymer and pharmaceutical fabrication techniques known in the art. For example, drug (with or without a biodegradable material) can be in solid form and then formed into the shape of the tissue-penetrating member 40 using molding, compaction or other like method with one or more binding agents added. Alternatively, drug and/or drug preparation may be in solid or liquid form and then added to the biodegradable material in liquid form with the mixture then formed into the penetrating member 40 using molding or other forming method known in the polymer arts.

Desirably, embodiments of the tissue-penetrating member 40 comprising a drug or other therapeutic agent and degradable material are formed at temperatures that do not produce any substantial thermal degradation of the drug (or other therapeutic agent) including drugs such as various peptides and proteins. This can be achieved through the use of room-temperature curing polymers and room temperature molding and solvent evaporation techniques known in the art. In particular embodiments, the amount of thermally degraded drug or other therapeutic agent within the tissue-penetrating member is desirably less than about 10% by weight and more preferably, less than 5% and still more preferably less than 1%. The thermal degradation temperature(s) for a particular drug are either known or can be determined using methods known in the art and then this temperature can be used to select and adjust the particular polymer processing methods (e.g., molding, curing. solvent evaporation methods etc.) to minimize the temperatures and associated level of drug thermal degradation.

After medication delivery, swallowable capsule 24 (including some or all of the pressure sensor 26, the control module 28, and the drug delivery modules 34) can pass from the antrum through the intestinal tract including the small and large intestine and be ultimately excreted. For embodiments of the capsule 24 having biodegradable seams or other biodegradable portions, the capsule is degraded in the intestinal tract into smaller pieces, to facilitate passage through and excretion from the intestinal tract. In particular embodiments having biodegradable tissue-penetrating needles/members 40, should the needle get stuck in the wall of the stomach, intestine (small or other large) or other location in the GI tract, the needle will biodegrade, releasing the capsule 24 from the stomach or intestinal wall.

One or more embodiments of the above methods can be used for the delivery of preparations containing therapeutically effective amounts of a variety of drugs and other therapeutic agents to treat a variety of diseases and conditions. These include a number of large molecule peptides and proteins that would otherwise require injection due to chemical degradation and/or deactivation in the stomach or intestines including, e.g., antibodies including various monoclonal antibodies such as tnf alfa antibodies, growth hormone, parathyroid hormone, insulin, interferons and other like compounds. Suitable drugs and other therapeutic agents that can be delivered by embodiments of the present invention include various immuchemo therapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents (e.g., Furosemide), antimigraine medication (sumatriptan), immune suppression agents (e.g., cyclosporine) and anti-parasitic agents such as various anti-malarial agents. The dosage of the particular drug can be titrated for the patient's weight, age or other parameter. Also, the drug to achieve a desired or therapeutic effect (e.g., insulin for blood glucose regulation, Furosemide for anti-seizure) can be less than the amount required should the drug have been delivered by conventional oral delivery (e.g., a swallowable pill that is digested in the stomach and absorbed through the wall of the small intestine). This is due to the fact that there is no degradation of the drug by acid and other digestive fluids in the stomach and the fact that all, as opposed to only a portion of the drug is delivered into the wall of the small intestine (or other lumen in the gastro-intestinal tract, e.g., large intestine, stomach, etc.). Depending upon the drug, the dose delivered in preparation can be in the range from 5% to 100% of a dose delivered by conventional oral delivery means to achieve a desired therapeutic effect (e.g., blood glucose regulation, seizure regulation, etc.) with even lower amounts contemplated. The particular dose reduction can be titrated based upon the particular drug, the condition to be treated, and the patient's weight, age and condition. For some drugs (with known levels of degradation in the intestinal tract) a standard dose reduction can be employed (e.g., 10 to 20%). Larger amounts of dose reduction can be used for drugs that are more prone to degradation and poor absorption. In this way, the potential toxicity and other side effects (e.g., gastric cramping, irritable bowel, hemorrhage, etc.) of a particular drug or drugs delivered by swallowable capsule 24 can be reduced because the ingested dose is lowered. This in turn, improves patient compliance because the patient has reduction both in the severity and incidence of side effects. Additional benefits of embodiments employing dose reduction of drug include a reduced likelihood for the patient to develop a tolerance to the drug (requiring higher doses) and, in the case of antibiotics, for the patient to develop resistant strains of bacteria. Also, other levels of dose reduction can be achieved for patients undergoing gastric bypass operations and other procedures in which sections of the small intestine have been removed or its working (e.g., digestive) length effectively shortened.

In addition to delivery of a single drug, embodiments of swallowable drug delivery swallowable capsule 24 and methods of their use can be used to deliver a plurality of drugs for the treatment of multiple conditions or for the treatment of a particular condition (e.g., protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream, at about the same time. Due to difference in chemical makeup, molecular weight, etc., drugs can be absorbed through the intestinal wall at different rates, resulting in different pharmacokinetic distribution curves. Embodiments of the present invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations including drugs and therapeutic agents to provide treatment for a number of medical conditions and diseases. The medical conditions and diseases that can be treated with embodiments of the present invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia's (both atrial and ventricular), coronary ischemia anemia or other like condition. Still other conditions and diseases are also contemplated such as various autoimmune disorders including multiple sclerosis, Guillain Barre syndrome, ankylosing spondylitis, chronic inflammatory demyelinating polyneuropathy, multifocal motor neuropathy, lupus and other like conditions. Therapeutic agents for the latter conditions may include IgG and rituximab.

In many embodiments, the treatment of the particular disease or condition can be performed without the need for injecting the drug or other therapeutic agent (or other non-oral form of delivery such as suppositories) but instead, relying solely on the therapeutic agent(s) that is delivered into the wall of the antrum, small intestine or other portion of the GI tract. For example, diabetes or another glucose regulation disorder can be treated (e.g., by controlling blood glucose levels) solely through the use of insulin that is delivered into the wall of the antrum, small intestine without the need for the patient to ever inject insulin. Similarly, the patient need not take conventional oral forms of a drug or other therapeutic agent, but again rely solely on delivery into the wall of the antrum or small intestine using embodiments of the swallowable capsule. In other embodiments, the therapeutic agent(s) delivered into the wall of the small intestine can be delivered in conjunction with an injected dose of the agent(s). For example, the patient may take a daily dose of insulin or compound for blood glucose regulation using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods to determine the appropriate dosages). Also, for embodiments using therapeutic agents that can be delivered by conventional oral means, the dose delivered using embodiments of the swallowable capsule can be titrated below the dosage normally given for oral delivery of the agent since there is little or no degradation of the agent within the stomach or other portion of the intestinal tract (herein again standard dose response curve and other pharmacokinetic methods can be applied).

Various groups of embodiments of preparations containing one or more drugs or other therapeutic agents for the treatment of various diseases and conditions will now be described with references to dosages. It should be appreciated that these embodiments, including the particular therapeutic agents and the respective dosages, are exemplary and the preparation can comprise a number of other therapeutic agents described herein (as well as those known in the art) that are configured for delivery into a luminal wall in the gastro-intestinal tract (e.g., the small intestinal wall) using various embodiments of swallowable capsule 24. The dosages can be larger or smaller than those described and can be adjusted using one or more methods described herein or known in the art. In one group of embodiments, therapeutic agent preparation can comprise a therapeutically effective dose of insulin for the treatment of diabetes and other glucose regulation disorders. The insulin can be human or synthetically derived as is known in the art. In one embodiment, preparation can contain a therapeutically effective amount of insulin in the range of about 1-10 units (one unit being the biological equivalent of about 45.5 µg of pure crystalline insulin), with particular ranges of 2-4, 3-9, 4-9, 5-8 or 6-7. The amount of insulin in the preparation can be titrated based upon one or more of the following factors (herein, then "glucose control titration factors"): i) the patient's condition (e.g., type 1 vs. type II diabetes; ii) the patients previous overall level of glycemic control; iii) the patient's weight; iv) the patient's age; v) the frequency of dosage (e.g., once vs. multiple times a day); vi) time of day (e.g., morning vs. evening); vii) particular meal (breakfast vs. dinner); viii) content/glycemic index of a particular meal (e.g., meals having a high fat/lipid and sugar content (which tend to cause a rapid rise in blood sugar and thus have a higher glycemic index) vs. low fat and sugar content that do not (and thus have a lower glycemic index)); and ix) content of the patient's overall diet (e.g., amount of sugars and other carbohydrates, lipids and protein consumed daily).

In another group of embodiments, therapeutic agent preparation can comprise a therapeutically effective dose of one or more incretins for the treatment of diabetes and other glucose regulation disorders. Such incretins can include glucagon-like peptides 1 (GLP-1) and their analogues, and gastric inhibitory peptide (GIP). Suitable GLP-1 analogues include exenatide, liraglutide, albiglutide and taspoglutide as well as their analogues, derivatives and other functional equivalents. In one embodiment preparation can contain a therapeutically effective amount of exenatide in the range of about 1-10 µg, with particular ranges of 2-4, 4-6, 4-8 and 8-10 µg respectively. In another embodiment, the preparation can contain a therapeutically effective amount of liraglutide in the range of about 1-2 mg (milligrams), with particular ranges of 1.0 to 1.4, 1.2 to 1.6 and 1.2 to 1.8 mg respectively. One or more of the glucose control titration factors can be applied to titrate the dose ranges for exenatide, liraglutide or other GLP-1 analogue or incretin.

In yet another group of embodiments, the therapeutic agent preparation can comprise a combination of therapeutic agents for the treatment of diabetes and other glucose regulation disorders. Embodiments of such a combination can include therapeutically effective doses of incretin and biguanide compounds. The incretin can comprise one or more GLP-1 analogues described herein, such as exenatide and the biguanide can comprise metformin (e.g., that available under the Trademark of GLUCOPHAGE manufactured by Merck Santé S.A.S.) and its analogues, derivatives and other functional equivalents. In one embodiment, preparation can comprise a combination of a therapeutically effective amount of exenatide in the range of about 1-10 µg and a therapeutically effective amount of metformin in a range of about 1 to 3 grams. Smaller and larger ranges are also contemplated with one or more of the glucose control titration factors used to titrate the respective dose of exenatide (or other incretin) and metformin or other biguanide. Additionally, the dosages of the exenatide or other incretin and metformin or other biguanide can be matched to improve the level of glucose control for the patient (e.g., maintenance of blood glucose within normal physiological levels and/or a reduction in the incidence and severity of instances of hyperglycemia and/or hypoglycemia) for extended periods of time ranging from hours (e.g., 12) to a day to multiple days, with still longer periods contemplated. Matching of dosages can also be achieved by use of the glucose control regulation factors as well as monitoring of the patient's blood glucose levels for extended periods using glycosylated hemoglobin (known as hemoglobin A1c, HbA1c, A1C, or Hb1c) and other bioanalytes and measurements correlative to long term average blood glucose levels.

In still yet another group of embodiments, therapeutic agent preparation can comprise a therapeutically effective dose of growth hormone for the treatment of one or more growth disorders, as well as wound healing. In one embodiment, preparation can contain a therapeutically effective amount of growth hormone in the range of about 0.1-4 mg, with particular ranges of 0.1-1, 1-4, 1-2 and 2-4, with still larger ranges contemplated. The particular dose can be titrated based on one or more of the following: i) the particular condition to be treated and its severity (e.g., stunted growth, vs. wound healing); ii) the patient's weight; iii) the patient's age; and iv) the frequency of dosage (e.g., daily vs. twice daily).

In still yet another group of embodiments, therapeutic agent preparation can comprise a therapeutically effective dose of parathyroid hormone for the treatment osteoporosis or a thyroid disorder. In one embodiment, preparation can contain a therapeutically effective amount of parathyroid hormone in the range of about 1-40 µg, with particular ranges of 10-20, 20-30, 30-40 and 10-40 µg, with still larger ranges contemplated. The particular dose can be titrated based on one or more of the following: i) the particular condition to be treated and its severity (e.g., the degree of osteoporosis as determined by bone density measurements); ii) the patient's weight; iii) the patient's age; and iv) the frequency of dosage (e.g., daily vs. twice daily).

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The foregoing invention of various embodiments of the technology of the present disclosure has been presented for purposes of illustration and invention. It is not intended to limit the technology of the present disclosure to the precise forms disclosed. Many modifications, variations and refinements will be apparent to practitioners skilled in the art. For example, embodiments of the device can be sized and otherwise adapted for various pediatric and neonatal applications as well as various veterinary applications. They may also be adapted for the urinary tracts of both male and females. Further, those skilled in the art will recognize, or be able to ascertain using no more than routine experimentation, numerous equivalents to the specific devices and methods described herein. Such equivalents are considered to be within the scope of the present technology of the present disclosure and are covered by the appended claims below.

Elements, characteristics, or acts from one embodiment can be readily recombined or substituted with one or more elements, characteristics or acts from other embodiments to form numerous additional embodiments within the scope of the present invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A swallowable device for delivering a solid dosage therapeutic agent preparation to a patient, the device comprising:
   a swallowable capsule having a capsule wall;
   a solid dosage therapeutic agent preparation held inside the capsule;
   a propulsive driver within the capsule configured to advance the solid dosage therapeutic agent preparation through the capsule wall and into a wall of the gastrointestinal (GI) tract, wherein the propulsive driver comprises a combustible propellant and an igniter; and
   wherein the igniter is configured to ignite the combustible propellant in response to an external condition selected from moisture, temperature, pressure, pH, and proximity to a wall of the GI tract.

2. The device of claim 1, wherein the igniter is configured to ignite the combustible propellant in response to a change in the external condition.

3. The device of claim 1, further comprising a sensor embedded in the capsule wall and coupled to the igniter, wherein the sensor senses the value of the external condition and causes the igniter to ignite the combustible propellant when a threshold value of the external condition is reached.

4. The device of claim 3, wherein the sensor is electronic and produces an electrical signal representative of the sensed condition.

5. The device of claim 4, wherein the igniter comprises a trigger circuit that receives the signal representative of the sensed condition from the sensor and that generates an ignition current and delivers the ignition current to the combustible propellant.

6. The device of claim 5, wherein the trigger circuit includes a battery and a capacitor, wherein the battery charges the capacitor and the capacitor discharges the charge into the propellant.

7. The device of claim 6, wherein the trigger circuit further includes wire filaments embedded in the propellant, wherein the wire filaments produce heat sufficient to ignite the propellant as the current is discharged from the capacitor therethrough.

8. The device of claim 7, wherein the propellant comprises nitrocellulose.

9. The device of claim 3, wherein the sensor comprises a mechanical or fluidic sensor element on an external region of the swallowable capsule that changes state in response to a change in the external condition.

10. The device of claim 9, wherein the igniter comprises mechanical or fluidic igniter element that responds to a change of state of the mechanical or fluidic sensor and mechanically generates energy to ignite the combustible propellant.

11. The device of claim 1, wherein the propulsive driver comprises a piston and a cylinder, wherein the combustible propellant is at a bottom of the cylinder beneath the piston and the solid dosage therapeutic agent preparation is on an upper surface of the piston.

12. The device of claim 11, wherein the propellant comprises a layer of nitrocellulose formed along the bottom of the cylinder.

13. The device of claim 12, wherein the layer of nitrocellulose comprises from 0.1 gm to 0.5 gm of nitrocellulose.

14. The device of claim 1, wherein the solid dosage therapeutic agent preparation comprises an active agent compressed with at least one of an excipient or a binder into an elongate member having a tapered, sharpened, or honed tip.

15. The device of claim 1, wherein the capsule wall comprises a cylindrical shell.

16. The device of claim 1, wherein at least a portion of the capsule wall is degradable in the gastrointestinal tract.

17. The device of claim 16, wherein at least a portion of the capsule wall is degradable in the patient's intestinal tract.

18. The device of claim 17, wherein the at least a portion of the capsule wall degrades at a pH equal to or greater than about 6.5.

19. The device of claim 1, wherein the solid dosage therapeutic agent preparation comprises a first solid dosage therapeutic agent preparation and a second solid dosage therapeutic agent preparation; the device further comprising:
   a second propulsive driver configured to drive the second solid dosage therapeutic agent preparation in a direction different from the first solid dosage therapeutic agent preparation.

20. The device of claim 19, wherein the propulsive driver and the second propulsive driver are configured to drive the respective first solid dosage therapeutic agent preparation and second solid dosage therapeutic agent preparation in at least two diametrically opposed directions.

21. A method for delivering a therapeutic agent into a wall of a patient's intestinal tract, the method comprising:
   providing a swallowable capsule having a therapeutic agent preparation held therein;
   ingesting by the patient of the swallowable capsule;
   passing the capsule through an initial portion of the patient's gastrointestinal (GI) tract while maintaining the therapeutic agent preparation therein;
   igniting a combustible propellant within the capsule in response to an external condition within the GI tract; and
   injecting, by the ignited propellant, the therapeutic agent from the capsule into a wall of the GI tract.

22. A swallowable device for delivering a therapeutic agent preparation into an antral wall of a patient's stomach, the device comprising:
   a capsule sized to pass through the patient's gastrointestinal tract, the capsule having a wall including opposed side portions and opposed end portions, the capsule having an elongated shape and being configured to longitudinally orient within the stomach at the antral wall during a peristaltic contraction of the stomach such that a side portion of the capsule wall is adjacent a wall of the antrum;

a therapeutic preparation in the capsule, the preparation comprising a therapeutic agent and shaped as a tissue-penetrating member;

a sensor disposed in a side wall portion of the capsule wall, the sensor configured to sense a condition external to the capsule and generate an electrical output in response to sensing an external condition corresponding to a peristaltic contraction of the stomach;

an ejector operatively coupled to the tissue-penetrating member and responsive to the output from the sensor, the ejector configured to trigger combustion of a propellant to eject the tissue-penetrating member through the capsule into the antral wall; and a logic circuit configured to analyze the electrical output from the sensor and generate a trigger signal when a change in the external condition is detected.

\* \* \* \* \*